US012706180B2

(12) United States Patent
Stram

(10) Patent No.: US 12,706,180 B2
(45) Date of Patent: Aug. 11, 2026

(54) SYSTEM AND METHOD FOR MANAGEMENT OF COMPRESSED SEQUENCING FILES

(71) Applicant: Personalis, Inc., Fremont, CA (US)

(72) Inventor: Alexander Halley Stram, Altadena, CA (US)

(73) Assignee: Personalis, Inc., Fremont, CA (US)

( * ) Notice: Subject to any disclaimer, the term of this patent is extended or adjusted under 35 U.S.C. 154(b) by 0 days.

(21) Appl. No.: 19/251,587

(22) Filed: Jun. 26, 2025

(65) Prior Publication Data

US 2026/0004886 A1 Jan. 1, 2026

Related U.S. Application Data

(60) Provisional application No. 63/665,079, filed on Jun. 27, 2024.

(51) Int. Cl.

| | |
|---|---|
| ***G16B 50/50*** | (2019.01) |
| ***G06F 16/174*** | (2019.01) |
| ***G06N 3/04*** | (2023.01) |
| ***G16B 20/00*** | (2019.01) |
| ***G16B 30/10*** | (2019.01) |
| ***G16B 50/20*** | (2019.01) |

(52) U.S. Cl.
CPC ........... *G16B 50/50* (2019.02); *G06F 16/174* (2019.01); *G06N 3/04* (2013.01); *G16B 20/00* (2019.02); *G16B 30/10* (2019.02); *G16B 50/20* (2019.02)

(58) Field of Classification Search
CPC ........ G16B 50/50; G16B 30/10; G16B 20/00; G16B 50/20; G16B 50/30; G06N 3/04; G06F 16/174
USPC ............................................... 341/50, 51, 87
See application file for complete search history.

(56) References Cited

U.S. PATENT DOCUMENTS 4,458,066 A 7/1984 Caruthers et al.
4,683,202 A 7/1987 Mullis
4,988,617 A 1/1991 Landegren et al.
(Continued)

FOREIGN PATENT DOCUMENTS

CN 105044108 A 11/2015
CN 109903811 A 6/2019
(Continued)

OTHER PUBLICATIONS

Ralph et al. "Consistency of VDJ rearrangement and substitution parameters enables accurate B cell receptor sequence annotation." PLoS computational biology 12.1 (2016): 1-25.
(Continued)

*Primary Examiner* — Khai M Nguyen
(74) *Attorney, Agent, or Firm* — Orrick , Herrington & Sutcliffe, LLP

(57) ABSTRACT

Systems and methods for management of storing and analyzing genetic sequencing data. In some embodiments disclosed herein, a method for converting a compressed SAM file back into a raw FASTQ file, wherein the information of the raw FASTQ file is substantively identical to that which was stored in the original FASTQ file from which the compressed SAM file is based is provided. The method advantageously enables storage of the smaller compressed SAM files for reliable, efficient reconstruction of the original FASTQ file when needed.

20 Claims, 6 Drawing Sheets

(56) References Cited

U.S. PATENT DOCUMENTS 5,143,854 A 9/1992 Pirrung et al.
5,242,794 A 9/1993 Whiteley et al.
5,299,491 A 4/1994 Kawada
5,382,510 A 1/1995 Levine et al.
5,403,708 A 4/1995 Brennan et al.
5,412,087 A 5/1995 McGall et al.
5,432,065 A 7/1995 Fuller
5,472,672 A 12/1995 Brennan
5,494,810 A 2/1996 Barany et al.
5,641,658 A 6/1997 Adams et al.
5,928,907 A 7/1999 Woudenberg et al.
6,015,674 A 1/2000 Woudenberg et al.
6,045,996 A 4/2000 Cronin et al.
6,156,504 A 12/2000 Gocke et al.
6,420,117 B1 7/2002 Wessler et al.
6,582,938 B1 6/2003 Su et al.
6,754,655 B1 6/2004 Segal
6,818,395 B1 11/2004 Quake et al.
7,169,560 B2 1/2007 Lapidus et al.
7,211,390 B2 5/2007 Rothberg et al.
7,211,654 B2 5/2007 Gao et al.
7,244,559 B2 7/2007 Rothberg et al.
7,264,929 B2 9/2007 Rothberg et al.
7,280,922 B2 10/2007 Mei et al.
7,282,337 B1 10/2007 Harris
7,300,788 B2 11/2007 Matsuzaki et al.
7,323,305 B2 1/2008 Leamon et al.
7,335,762 B2 2/2008 Rothberg et al.
7,361,488 B2 4/2008 Fan et al.
7,534,561 B2 5/2009 Sana et al.
7,582,420 B2 9/2009 Oliphant et al.
7,785,783 B2 8/2010 Morley et al.
7,803,550 B2 9/2010 Makarov et al.
8,026,094 B2 9/2011 Green et al.
8,133,719 B2 3/2012 Drmanac et al.
8,140,270 B2 3/2012 Kingsmore et al.
8,296,076 B2 10/2012 Fan et al.
8,318,430 B2 11/2012 Chuu et al.
8,323,897 B2 12/2012 Andersen et al.
8,415,101 B2 4/2013 Garner
8,417,459 B2 4/2013 Reese et al.
8,532,930 B2 9/2013 Rabinowitz et al.
8,589,175 B2 11/2013 Glauser et al.
8,785,353 B2 7/2014 Van Eijk et al.
8,862,410 B2 10/2014 Hatchwell et al.
9,051,602 B2 6/2015 Oliphant et al.
9,109,256 B2 8/2015 Shuber
9,128,861 B2 9/2015 Bartha et al.
9,183,496 B2 11/2015 Harris et al.
9,228,232 B2 1/2016 Faham et al.
9,329,170 B2 5/2016 Clarke et al.
9,416,422 B2 8/2016 Cheung
9,453,257 B2 9/2016 Hoyal-Wrightson et al.
9,512,485 B2 12/2016 Richardson et al.
9,523,121 B2 12/2016 Spier et al.
9,725,755 B2 8/2017 Poole et al.
9,727,692 B2 8/2017 Harris et al.
9,745,626 B2 8/2017 Bartha et al.
9,909,186 B2 3/2018 Schuetz et al.
10,017,810 B2 7/2018 Iafrate et al.
10,032,000 B1 7/2018 Harris et al.
10,125,399 B2 11/2018 West
10,174,375 B2 1/2019 Lo et al.
10,255,330 B2 4/2019 Chandratillake et al.
10,262,103 B2 4/2019 Lehrer et al.
10,266,890 B2 4/2019 Bartha et al.
10,344,318 B2 7/2019 May et al.
10,415,091 B2 9/2019 Bartha et al.
10,450,611 B2 10/2019 West et al.
10,590,468 B2 3/2020 Pedersen et al.
10,597,717 B2 3/2020 Maguire et al.
10,711,306 B2 7/2020 Shiina et al.
10,738,355 B2 8/2020 Sahin et al.
10,741,269 B2 8/2020 Chudova et al.
10,801,064 B2 10/2020 West et al.
10,801,070 B2 10/2020 Clement et al.
10,900,088 B2 1/2021 Volgelstein et al.
11,047,006 B2 6/2021 Salk et al.
11,062,789 B2 7/2021 Chiu et al.
11,124,824 B2 9/2021 Sarwal et al.
11,142,797 B2 10/2021 Moynahan et al.
11,155,867 B2 10/2021 Bartha et al.
11,286,530 B2 3/2022 Rabinowitz et al.
11,345,968 B2 5/2022 Mortimer et al.
11,840,730 B1 12/2023 Porreca et al.
12,203,142 B2 1/2025 Babiarz et al.
2002/0006615 A1 1/2002 Goldsborough et al.
2002/0164629 A1 11/2002 Quake et al.
2003/0022200 A1 1/2003 Vissing et al.
2003/0096011 A1 5/2003 Tracy et al.
2003/0099964 A1 5/2003 Patil et al.
2003/0100995 A1 5/2003 Loraine et al.
2003/0220777 A1 11/2003 Kitchen et al.
2005/0042668 A1 2/2005 Perlin
2005/0086035 A1 4/2005 Peccoud et al.
2005/0125474 A1 6/2005 Pednault
2005/0250125 A1 11/2005 Novakoff
2005/0260645 A1 11/2005 Green et al.
2006/0184489 A1 8/2006 Weiner et al.
2006/0278241 A1 12/2006 Ruano
2007/0111247 A1 5/2007 Stephens et al.
2007/0184436 A1 8/2007 Myerson et al.
2008/0096766 A1 4/2008 Lee
2008/0305473 A1 12/2008 Chowdary et al.
2009/0026082 A1 1/2009 Rothberg et al.
2009/0029364 A1 1/2009 Zirwes et al.
2009/0127589 A1 5/2009 Rothberg et al.
2009/0183268 A1 7/2009 Kingsmore
2009/0191565 A1 7/2009 Lapidus et al.
2009/0326832 A1 12/2009 Heckerman et al.
2010/0029498 A1 2/2010 Gnirke et al.
2010/0035252 A1 2/2010 Rothberg et al.
2010/0042438 A1 2/2010 Moore et al.
2010/0137143 A1 6/2010 Rothberg et al.
2010/0188073 A1 7/2010 Rothberg et al.
2010/0197507 A1 8/2010 Rothberg et al.
2010/0282617 A1 11/2010 Rothberg et al.
2010/0300559 A1 12/2010 Schultz et al.
2010/0300895 A1 12/2010 Nobile et al.
2010/0301398 A1 12/2010 Rothberg et al.
2010/0304982 A1 12/2010 Hinz et al.
2011/0004413 A1 1/2011 Carnevali et al.
2011/0009296 A1 1/2011 Kain et al.
2011/0105353 A1 5/2011 Lo et al.
2011/0184896 A1 7/2011 Guyon
2012/0015050 A1 1/2012 Abkevich et al.
2012/0058480 A1 3/2012 Lewis et al.
2012/0077682 A1 3/2012 Bowcock et al.
2012/0116688 A1 5/2012 Mishra et al.
2012/0143512 A1 6/2012 Reese et al.
2012/0208706 A1 8/2012 Downing et al.
2012/0270206 A1 10/2012 Ginns et al.
2012/0270212 A1 10/2012 Rabinowitz et al.
2012/0295810 A1 11/2012 Quake et al.
2013/0073217 A1 3/2013 Dewey et al.
2013/0090908 A1 4/2013 Dewey et al.
2013/0096011 A1 4/2013 Rava et al.
2013/0102477 A1 4/2013 Morin et al.
2013/0124100 A1 5/2013 Drmanac et al.
2013/0173177 A1 7/2013 Pelleymounter
2013/0178389 A1 7/2013 Lapidus et al.
2013/0261196 A1 10/2013 Diamond et al.
2013/0296535 A1 11/2013 Church et al.
2013/0311448 A1 11/2013 Thompson
2013/0332081 A1 12/2013 Reese et al.
2014/0186827 A1 7/2014 Pieprzyk et al.
2014/0200147 A1 7/2014 Bartha et al.
2015/0051087 A1 2/2015 Rabinowitz et al.
2015/0057160 A1 2/2015 Breuer et al.
2015/0066824 A1 3/2015 Harris et al.
2016/0019341 A1 1/2016 Harris et al.
2016/0032396 A1 2/2016 Diehn et al.
2016/0041987 A1 2/2016 Lapir et al.
2016/0092631 A1 3/2016 Yandell et al.

(56) References Cited

U.S. PATENT DOCUMENTS

2016/0122831 A1 5/2016 West
2016/0283484 A1 9/2016 Chandratillake et al.
2017/0060896 A1 3/2017 Ito et al.
2017/0147597 A1 5/2017 Leighton et al.
2017/0166981 A1 6/2017 Craig et al.
2017/0199961 A1 7/2017 Yelensky et al.
2017/0253921 A1 9/2017 Liu et al.
2017/0316150 A1 11/2017 Deciu et al.
2017/0356053 A1 12/2017 Otto et al.
2018/0051338 A1 2/2018 West et al.
2018/0127807 A1 5/2018 Stahl et al.
2018/0203974 A1 7/2018 Venn
2018/0258489 A1 9/2018 Danenberg
2018/0282801 A1 10/2018 Zhao et al.
2018/0363066 A1 12/2018 Chalmers et al.
2019/0127803 A1 5/2019 Hacohen et al.
2019/0153541 A1 5/2019 Lo et al.
2019/0189242 A1 6/2019 Angiuoli et al.
2019/0211406 A1 7/2019 Babiarz et al.
2019/0285518 A1 9/2019 Lu et al.
2019/0346442 A1 11/2019 Carr et al.
2020/0024669 A1 1/2020 Spetzler et al.
2020/0048711 A1 2/2020 Snyder
2020/0058377 A1 2/2020 Bagaev et al.
2020/0105378 A1 4/2020 Abelin et al.
2020/0149097 A1 5/2020 Otto et al.
2020/0157604 A1 5/2020 Plagnol et al.
2020/0202224 A1 6/2020 Lanman et al.
2020/0258597 A1 8/2020 Perera
2020/0258601 A1 8/2020 Lau
2020/0392584 A1 12/2020 Almogy et al.
2021/0054452 A1 2/2021 West et al.
2021/0062258 A1 3/2021 Bartha et al.
2021/0062276 A1 3/2021 West
2021/0210205 A1 7/2021 Drake et al.
2021/0238677 A1 8/2021 Bartha et al.
2021/0257052 A1 8/2021 Rooyen et al.
2021/0304841 A1* 9/2021 Renzi .................... G16B 25/10
2021/0363586 A1 11/2021 Artsiomenka et al.
2021/0398609 A1 12/2021 Sigurjonsson et al.
2022/0004847 A1 1/2022 Mapiye et al.
2022/0064733 A1 3/2022 Alexander et al.
2022/0073985 A1 3/2022 Nerenberg et al.
2022/0081716 A1 3/2022 West et al.
2022/0195530 A1 6/2022 Diehn et al.
2022/0344005 A1 10/2022 Molyneaux et al.
2024/0134825 A1* 4/2024 Nazari ................ G06F 16/1744

FOREIGN PATENT DOCUMENTS

EP 0 281 927 B1 6/1995
EP 1 342 794 B1 12/2005
EP 2 861 788 B1 10/2018
EP 3 212 808 B1 3/2022
WO 2000/018957 A1 4/2000
WO 2005/098046 A2 10/2005
WO 2007/055244 A1 5/2007
WO 2010/054589 A1 5/2010
WO 2011/050341 A1 4/2011
WO 2011/057061 A1 5/2011
WO 2011/057094 A1 5/2011
WO 2011/091046 A1 7/2011
WO 2011/149534 A2 12/2011
WO 2011/160063 A2 12/2011
WO 2011/160206 A1 12/2011
WO 2012/142611 A2 10/2012
WO 2014/053295 A1 4/2014
WO 2014/062717 A1 4/2014
WO 2014/113204 A1 7/2014
WO 2014/207245 A1 12/2014
WO 2015/051275 A1 4/2015
WO 2015/095889 A2 6/2015
WO 2016/070131 A1 5/2016
WO 2017/205823 A1 11/2017
WO 2018/053365 A1 3/2018
WO 2018/064547 A1 4/2018
WO 2018/144782 A1 8/2018
WO 2018/195357 A1 10/2018
WO 2018/222883 A1 12/2018
WO 2019/168984 A1 9/2019
WO 2019/226939 A1 11/2019
WO 2019/231856 A1 12/2019
WO 2020/132586 A1 6/2020
WO 2020/168008 A1 8/2020
WO 2020/252721 A1 12/2020
WO 2021/016089 A1 1/2021
WO 2022/046947 A1 3/2022

OTHER PUBLICATIONS

Riaz et al. "Tumor and microenvironment evolution during immunotherapy with nivolumab." Cell 171.4 (2017): 934-949.
Richter, S. "Fecal DNA screening in colorectal cancer." Canadian Journal of Gastroenterology and Hepatology 22.7 (2008): 631-633.
Riester et al. "PureCN: copy number calling and SNV classification using targeted short read sequencing." Source Code for Biology and Medicine 11.13 (2016): 1-13.
Roberts et al. "The predictive capacity of personal genome sequencing." Science translational medicine 4.133 (2012): 1-9.
Robinson et al. "Strategies for exome and genome sequence data analysis in disease-gene discovery projects." Clinical genetics 80.2 (2011): 127-132.
Robinson et al. "The Human Phenotype Ontology: a tool for annotating and analyzing human hereditary disease." The American Journal of Human Genetics 83.5 (2008): 610-615.
Rogozin et al. "Somatic mutation hotspots correlate with DNA polymerase n error spectrum." Nature immunology 2.6 (2001): 530-536.
Rosenfeld et al. "Novel multi-nucleotide polymorphisms in the human genome characterized by whole genome and exome sequencing." Nucleic acids research 38.18 (2010): 6102-6111.
Ross et al. "Characterizing and measuring bias in sequence data." Genome biology 14 (2013): 1-20.
Ross et al. "Whole cancer genome sequencing by next-generation methods." American journal of clinical pathology 136.4 (2011): 527-539.
Ross, D. "Introduction to oncogenes and molecular cancer medicine." Springer Science & Business Media (1998): 1-10.
Saeys et al. "A review of feature selection techniques in bioinformatics." Bioinformatics 23.19 (2007): 2507-2517.
Sahraeian et al. "Deep convolutional neural networks for accurate somatic mutation detection." Nature communications 10.1 (2019): 1-10.
Saiki et al. "Analysis of enzymatically amplified beta-globin and HLA-DQ alpha DNA with allele-specific oligonucleotide probes." Nature 324.6093 (1986): 163-166.
Sambrook et al. "Molecular cloning: A Laboratory Manual." 4th ed, 448 (2012): 1-26.
Samuels et al. "Genetic mosaics and the germ line lineage." Genes 6.2 (2015): 216-237.
Sandri et al. "Apoptosis, DNA damage and ubiquitin expression in normal and mdx muscle fibers after exercise." FEBS letters 373.3 (1995): 291-295.
Saunders et al. "Strelka: accurate somatic small-variant calling from sequenced tumor normal sample pairs." Bioinformatics 28.14 (2012): 1811-1817.
Schmitt et al. "Detection of ultra-rare mutations by next-generation sequencing." Proceedings of the National Academy of Sciences 109.36 (2012): 14508-14513.
Schwarzenbach et al. "Detection and monitoring of cell-free DNA in blood of patients with colorectal cancer." Annals of the New York Academy of Sciences 1137.1 (2008): 190-196.
Scitable. "Mendelian Trait." Scitable by Nature Education, 2014. Retrieved from the Internet: <URL:https://web.archive.org/web/20140825124707/https://www.nature.com/scitable/definition/mendelian-trait-174/>, 2 pages.

(56) References Cited

OTHER PUBLICATIONS

Sequence Alignment/Map Format Specification, Manual [online], The SAM/BAM Format Specification Working Group, 2024. Retrieved from the Internet: <URL:https://samtools.github.io/hts-specs/SAMv1.pdf>, 23 pages.
Shapiro, E. "The human cell lineage flagship initiative." Lineage-flagship.eu, 2010. Retrieved from the Internet: <URL:http://www.lineage-flagship.eu/>, 1 page.
Shaw et al. "Genomic analysis of circulating cell-free DNA infers breast cancer dormancy." Genome research 22.2 (2012): 220-231.
Shendure et al. "Next-generation DNA sequencing." Nature biotechnology 26.10 (2008): 1135-1145.
Shigemizu et al. "A practical method to detect SNVs and indels from whole genome and exome sequencing data." Scientific reports 3.1 (2013): 1-6.
Shigemizu et al. "A practical method to detect SNVs and indels from whole genome and exome sequencing data." Supplementary Information. Scientific reports 3.1 (2013): 1-3.
Shim et al. "HLA-corrected tumor mutation burden and homologous recombination deficiency for the prediction of response to PD-(L) 1 blockade in advanced non-small-cell lung cancer patients." Annals of Oncology 31.7 (2020): 902-911.
Sims et al. "Sequencing depth and coverage: key considerations in genomic analyses." Nature Reviews Genetics 15.2 (2014): 121-132.
Singleton et al. "Phevor combines multiple biomedical ontologies for accurate identification of disease-causing alleles in single individuals and small nuclear families." The American Journal of Human Genetics 94.4 (2014): 599-610.
Smyth, G. "Limma: linear models for microarray data." Bioinformatics and computational biology solutions using R and Bioconductor. New York, NY: Springer New York (2005): 397-420.
Snyder et al. "Genetic Basis for Clinical Response to CTLA-4 Blockade in Melanoma." New England Journal of Medicine (2014): 1-11.
Song et al. "A reference methylome database and analysis pipeline to facilitate integrative and comparative epigenomics." PloS one 8.12 (2013): 1-9.
Soni et al. "Progress toward ultrafast DNA sequencing using solid-state nanopores." Clinical chemistry 53.11 (2007): 1996-2001.
Spalding et al. "Retrospective birth dating of cells in humans." Cell 122.1 (2005): 133-143.
Stemmer et al. "Single-step assembly of a gene and entire plasmid from large numbers of oligodeoxyribonucleotides." Gene 164.1 (1995): 49-53.
Stevanovic et al. "Landscape of immunogenic tumor antigens in successful immunotherapy of virally induced epithelial cancer." Science 356.6334 (2017): 200-205.
Sudhakar et al. "Characterization of clonal immunoglobulin heavy (IGH) VDJ gene rearrangements and the complementarity-determining region in South Indian patients with precursor B-cell acute lymphoblastic leukemia." Blood research 52.1 (2017): 55-61.
Sulston et al. "Post-embryonic cell lineages of the nematode, Caenorhabditis elegans." Developmental biology 56.1 (1977): 110-156.
Sulston et al. "The embryonic cell lineage of the nematode Caenorhabditis elegans." Developmental biology 100.1 (1983): 64-119.
Summerer et al. "Targeted high throughput sequencing of a cancer-related exome subset by specific sequence capture with a fully automated microarray platform." Genomics 95.4 (2010): 241-246.
Sun et al. "Optimized data representation and convolutional neural network model for predicting tumor purity." bioRxiv (2019): 1-9.
Sung et al. "Assessment of intratumoral heterogeneity with mutations and gene expression profiles." PLoS One 14.7 (2019): 1-15.
SVBio. "SVBio's Services." Company Information [online], SVBio, 2014. Retrieved from the Internet: <URL:http:www.svbio.com/service-offerings/current-services>, 1 page.
Swanton, C. "Plasma-derived tumor DNA analysis at whole-genome resolution." Clinical Chemistry 59.1 (2013): 6-8.
Teer et al. "Exome sequencing: the sweet spot before whole genomes." Human molecular genetics 19.R2 (2010): R145-R151.
Tests and Procedures: Urine cytology, Definition [online], Mayo Clinic, 2014 [retrieved on Dec. 1, 2015]. Retrieved from the Internet: <URL:http://www.mayoclinic.org/tests-procedures/urine-cytology/basics/definition/prc-20020408>, 3 pages.
Tewhey et al. "Microdroplet-based PCR enrichment for large-scale targeted sequencing." Nature biotechnology 27.11 (2009): 1025-1031.
Tug et al. "Exercise-induced increases in cell free DNA in human plasma originate predominantly from cells of the haematopoietic lineage." Exercise immunology review 21 (2015): 164-173.
Turajlic et al. "Whole genome sequencing of matched primary and metastatic acral melanomas." Genome research 22.2 (2012): 196-207.
Turajlic et al. "Whole genome sequencing of matched primary and metastatic acral melanomas." Supplementary Figures. Genome research 22.2 (2012): 1-43.
Turajlic et al. "Whole genome sequencing of matched primary and metastatic acral melanomas." Supplementary Tables. Genome research 22.2 (2012): 1-532.
Vaisvila et al. "EM-seq: detection of DNA methylation at single base resolution from picograms of DNA." BioRxiv (2019): 1-38.
Valadi et al. "Exosome-mediated transfer of mRNAs and microRNAs is a novel mechanism of genetic exchange between cells." Nature cell biology 9.6 (2007): 654-659.
Vale et al. "Does anti-EGFR therapy improve outcome in advanced colorectal cancer? A systematic review and meta-analysis." Cancer treatment reviews 38.6 (2012): 618-625.
Van Driel et al. "A text-mining analysis of the human phenome." European journal of human genetics 14.5 (2006): 535-542.
Varscan. "Variant Detection in Massively Parallel Sequencing Data." VarScan, 2009. Retrieved from the Internet: <URL:www.varscan.sourceforge.net.>, 4 pages.
Vasan, R. "Biomarkers of cardiovascular disease: molecular basis and practical considerations." Circulation 113.19 (2006): 2335-2362.
Velculescu et al. "Characterization of the yeast transcriptome." Cell 88.2 (1997): 243-251.
Velculescu et al. "Serial analysis of gene expression." Science 270.5235 (1995): 484-487.
Vietsch et al. "Circulating DNA and micro-RNA in patients with pancreatic cancer." Pancreatic disorders & therapy 5.2 (2015): 1-17.
Vinay et al. "Immune evasion in cancer: Mechanistic basis and therapeutic strategies." Seminars in cancer biology. vol. 35. Academic Press (2015): S185-S198.
Vincent et al. "Helicase-dependent isothermal DNA amplification." EMBO reports 5.8 (2004): 795-800.
Vos et al. "AFLP: a new technique for DNA fingerprinting." Nucleic acids research 23.21 (1995): 4407-4414.
Wagle et al. "High-throughput detection of actionable genomic alterations in clinical tumor samples by targeted, massively parallel sequencing." Cancer discovery 2.1 (2012): 82-93.
Walker et al. "Strand displacement amplification an isothermal, in vitro DNA amplification technique." Nucleic acids research 20.7 (1992): 1691-1696.
Wang et al. "Clonal evolution in breast cancer revealed by single nucleus genome sequencing." Nature 512.7513 (2014): 155-160.
Wang, K. "ANNOVAR Documentation." Datasheet [online], ANNOVAR, 2010. Retrieved from the Internet: <URL: https://annovar.openbioinformatics.org/en/latest/>, 7 pages.
Warren et al. "Targeted assembly of short sequence reads." PloS one 6.5 (2011): 1-6.
Wasserstrom et al. "Reconstruction of cell lineage trees in mice." PloS one 3.4 (2008): 1-11.
Westin et al. "Anchored multiplex amplification on a microelectronic chip array." Nature Biotechnology 18.2 (2000): 199-204.
Wikipedia. "Gradient boosting." Wikipedia, 2020. Retrieved from the Internet: <URL:https://en.wikipedia.org/w/index.php?title=Gradient_boosting&oldid=957594903>, 8 pages.
Wright et al. "The use of cell-free fetal nucleic acids in maternal blood for non-invasive prenatal diagnosis." Human reproduction update 15.1 (2009): 139-151.

(56) References Cited

OTHER PUBLICATIONS

Xiao et al. "Identifying mRNA, microRNA and protein profiles of melanoma exosomes." PLoS One 7.10 (2012): 1-15.
Yang et al. "Clinical whole-exome sequencing for the diagnosis of mendelian disorders." New England Journal of Medicine 369.16 (2013): 1502-1511.
Yeung et al. "LOH in the HLA class I region at 6p21 is associated with shorter survival in newly diagnosed adult glioblastoma." Clinical Cancer Research 19.7 (2013): 1816-1826.
Yi et al. "Sequencing of fifty human exomes reveals adaptation to high altitude." Science 329.5987 (2010): 75-78.
Yu et al. "Chapter 3 MarkDuplicates: A practical introduction to GATK 4 on Biowulf." GATK, 2021 [retrieved on Jun. 16, 2022]. Retrieved from the Internet: <URL:https://hpc.nih.gov/training/gatk_tutorial/markdup.html>, 6 pages.
Yu et al. "Mung bean nuclease treatment increases capture specificity of microdroplet-PCR based targeted DNA enrichment." Plos one 9.7 (2014): 1-7.
Zeerleder, S. "The struggle to detect circulating DNA." Critical Care 10 (2006): 1-3.
Zheng et al. "Estimating and accounting for tumor purity in the analysis of DNA methylation data from cancer studies." Genome biology 18 (2017): 1-14.
Griewank et al. "Genetic alterations and personalized medicine in melanoma: progress and future prospects." Journal of the National Cancer Institute 106.2 (2014): 1-17.
Ju et al. "Extensive genomic and transcriptional diversity identified through massively parallel DNA and RNA sequencing of eighteen Korean individuals." Nature genetics, 43(8), pp. 745-752. Available at: https://doi.org/10.1038/ng.872. (2011).
Ju et al. "A transforming KIF5B and RET gene fusion in lung adenocarcinoma revealed from whole-genome and transcriptome sequencing." Genome Research, 22(3), pp. 436-445. Available at: https://doi.org/10.1101/gr.133645.111. (2011).
Seo et al. "The transcriptional landscape and mutational profile of lung adenocarcinoma." Genome Research, 22(11), pp. 2109-2119. Available at: https://doi.org/10.1101/gr.145144.112. (2012).
Shah et al. "Mutational evolution in a lobular breast tumour profiled at single nucleotide resolution." Nature, 461 (7265), pp. 809-813. Available at: https://doi.org/10.1038/nature08489. (2009).
Dawe et al. "Cell migration from baby to mother." Cell adhesion & migration 1.1 (2007): 19-27.
Dawson et al. "Analysis of circulating tumor DNA to monitor metastatic breast cancer." New England Journal of Medicine 368.13 (2013): 1199-1209.
De La Chapelle, A. "The incidence of Lynch syndrome." Familial cancer 4 (2005): 233-237.
De Mattos-Arruda et al. "Capturing intra-tumor genetic heterogeneity by de novo mutation profiling of circulating cell-free tumor DNA: a proof-of-principle." Annals of oncology 25.9 (2014): 1729-1735.
De Mattos-Arruda et al. "Circulating tumour cells and cell-free DNA as tools for managing breast cancer." Nature reviews Clinical oncology 10.7 (2013): 377-389.
Decathelineau et al. "The final step in programmed cell death: phagocytes carry apoptotic cells to the grave." Essays in biochemistry 39 (2003): 105-117.
Dewey et al. "Phased whole-genome genetic risk in a family quartet using a major allele reference sequence." PLoS genetics 7.9 (2011): 1-15.
Diaz et al. "Insights into therapeutic resistance from whole-genome analyses of circulating tumor DNA." Oncotarget 4.10 (2013): 1856-1857.
Diaz et al. "Liquid biopsies: genotyping circulating tumor DNA." Journal of clinical oncology 32.6 (2014): 579-586.
Diehl et al. "Detection and quantification of mutations in the plasma of patients with colorectal tumors." Proceedings of the National Academy of Sciences 102.45 (2005): 16368-16373.
Ding et al. "Genome remodelling in a basal-like breast cancer metastasis and xenograft." Nature 464.7291 (2010): 999-1005.
Dressman et al. "Transforming single DNA molecules into fluorescent magnetic particles for detection and enumeration of genetic variations." Proceedings of the National Academy of Sciences 100.15 (2003): 8817-8822.
Drmanac et al. "Human genome sequencing using unchained base reads on self-assembling DNA nanoarrays." Science 327.5961 (2010): 78-81.
EcSeq. "How to calculate the coverage for a NGS experiment." ecSeq Bioinformatics, 2019 [retrieved on Jul. 5, 2022]. Retrieved from the Internet: <URL:https://www.ecseq.com/support/ngs/how-to-calculate-the-coverage-for-a-sequencing-experiment>, 3 pages.
Ellinger et al. "The role of cell-free circulating DNA in the diagnosis and prognosis of prostate cancer." Urologic Oncology: Seminars and Original Investigations, Elsevier 29.2 (2011): 124-129.
Elsharawy et al. "Accurate variant detection across non-amplified and whole genome amplified DNA using targeted next generation sequencing." BMC genomics 13 (2012): 1-14.
Elshimali et al. "The clinical utilization of circulating cell free DNA (CCFDNA) in blood of cancer patients." International journal of molecular sciences 14.9 (2013): 18925-18958.
Esplin et al. "Personalized sequencing and the future of medicine: discovery, diagnosis and defeat of disease." Pharmacogenomics 15.14 (2014): 1771-1790.
Fahy et al. "Self-sustained sequence replication (3SR): an isothermal transcription-based amplification system alternative to PCR." Genome Research 1.1 (1991): 25-33.
Fairbrother et al. "RESCUE-ESE identifies candidate exonic splicing enhancers in vertebrate exons." Nucleic acids research 32 (2004): W187-W190.
FASTQ Format, Encyclopedia [online], Wikipedia, 2000. Retrieved from the Internet: <URL:https://en.wikipedia.org/wiki/FASTQ_format>, 11 pages.
Fishel et al. "Meta-analysis of gene expression data: a predictor-based approach." Bioinformatics 23.13 (2007): 1599-1606.
Fluidigm. "Specification Sheet for Access Array System." Datasheet [online], Fluidigm, 2012, 4 pages.
Forshew et al. "Noninvasive identification and monitoring of cancer mutations by targeted deep sequencing of plasma DNA." Science translational medicine 4.136 (2012): 1-13.
Forshew et al. "Noninvasive identification and monitoring of cancer mutations by targeted deep sequencing of plasma DNA." Supplementary Materials. Science translational medicine 4.136 (2012): 1-20.
Fox et al. "Accuracy of next generation sequencing platforms." Next generation, sequencing & applications 1 (2014): 1-9.
Freed et al. "Somatic mosaicism in the human genome." Genes 5.4 (2014): 1064-1094.
Freshney, R. "Culture of Animal Cells: A Manual of Basic Technique and Specialized Applications." Sixth Edition, Hoboken, New Jersey, John Wiley & Sons (2010): 1-42.
Frumkin et al. "Genomic variability within an organism exposes its cell lineage tree." PLoS computational biology 1.5 (2005): 382-394.
GATK. "Genome Analysis Toolkit: Variant Discovery in High-Throughput Sequencing Data." Broad Institutes: GATK, 2025. Retrieved from the Internet: <URL:https://gatk.broadinstitute.org/hc/en-us>, 2 pages.
Gilbert, S. "Developmental Biology Tenth Edition." Sunderland, MA, Sinauer Associates, Inc. (2014): 1-12.
Gnirke et al. "Solution hybrid selection with ultra-long oligonucleotides for massively parallel targeted sequencing." Nature biotechnology 27.2 (2009): 182-189.
Golob, J. "Mechanisms of cell fate acquisition in the differentiation of pluripotent stem cells." University of Washington (2009): 1-126.
Goris et al. "The immunogenetic architecture of autoimmune disease." Cold Spring Harbor perspectives in biology 4.3 (2012): 1-15.
Gottlieb et al. "The DiGeorge syndrome minimal critical region contains a goosecoid-like (GSCL) homeobox gene that is expressed early in human development." American journal of human genetics 60.5 (1997): 1194-1201.
Guan et al. "Application of next-generation sequencing in clinical oncology to advance personalized treatment of cancer." Chinese journal of cancer 31.10 (2012): 463-470.

(56) References Cited

OTHER PUBLICATIONS

Guo et al. "Exome sequencing generates high quality data in non-target regions." BMC genomics 13 (2012): 1-10.
Guo et al. "Exome sequencing generates high quality data in non-target regions." BMC genomics 13, Supplementary Tables, (2012): 1-803.
Guo et al. "Whole-genome and whole-exome sequencing of bladder cancer identifies frequent alterations in genes involved in sister chromatid cohesion and segregation." Nature genetics 45.12 (2013): 1459-1463.
Haferlach et al. "Mutations of the TP53 gene in acute myeloid leukemia are strongly associated with a complex aberrant karyotype." Leukemia 22.8 (2008): 1539-1541.
Hamfjord et al. "Differential expression of miRNAs in colorectal cancer: comparison of paired tumor tissue and adjacent normal mucosa using high-throughput sequencing." PloS one 7.4 (2012): 1-9.
Hiratani et al. "Replication timing and transcriptional control: beyond cause and effect part II." Current opinion in genetics & development 19.2 (2009): 142-149.
Hirschhorn et al. "Human intersex with chromosome mosaicism of type XY/XO: Report of a case." New England Journal of Medicine 263.21 (1960): 1044-1048.
Hohaus et al. "Cell-free circulating DNA in Hodgkin's and non-Hodgkin's lymphomas." Annals of oncology 20.8 (2009): 1408-1413.
Holstege et al. "Somatic mutations found in the healthy blood compartment of a 115-yr-old woman demonstrate oligoclonal hematopoiesis." Genome research 24.5 (2014): 733-742.
Hong et al. "Tracking the origins and drivers of subclonal metastatic expansion in prostate cancer." Nature communications 6.1 (2015): 1-12.
Huang et al. "Characterization of human plasma-derived exosomal RNAs by deep sequencing." BMC genomics 14 (2013): 1-14.
Huang et al. "Machine learning predicts individual cancer patient responses to therapeutic drugs with high accuracy." Scientific reports 8.1 (2018): 1-8.
Huang et al. "SMuRF: portable and accurate ensemble prediction of somatic mutations." Bioinformatics 35.17 (2019): 3157-3159.
Human Genome Overview GRCh37, Datasheet [online], Genome Reference Consortium, 2009 [retrieved on Sep. 12, 2022]. Retrieved from the Internet: <URL:https://www.ncbi.nlm.nih.gov/grc/human>, 2 pages.
Adessi et al. "Solid phase DNA amplification: characterisation of primer attachment and amplification mechanisms." Nucleic acids research 28.20 (2000): 1-8.
Agilent. "SureSelectXT Target Enrichment System for the Illumina Platform." Datasheet [online], Agilent Technologies, 2021. Retrieved from the Internet: <URL:https://www.agilent.com/cs/library/usermanuals/public/G7530-90000.pdf>, 102 pages.
Akey et al. "Haplotypes vs single marker linkage disequilibrium tests: what do we gain?" European Journal of Human Genetics 9.4 (2001): 291-300.
Albert et al. "Direct selection of human genomic loci by microarray hybridization." Nature methods 4.11 (2007): 903-905.
Alter et al. "Clinical and molecular features associated with biallelic mutations in FANCD1/BRCA2." Journal of medical genetics 44.1 (2007): 1-9.
Anderson et al. "Next generation DNA sequencing and the future of genomic medicine." Genes 1.1 (2010): 38-69.
Anonymous. "Cell Fate Map Adapted from Gilberts Developmental Biology, Fourth Edition, Figure 9.1." Stack Exchange: Biology, Apr. 16, 2014. Retrieved from the Internet: <URL:https://biology.stackexchange.com/questions/16555/where-does-the-fate-map-of-a-human-embryo-end>, 3 pages.
Anzar et al. "NeoMutate: an ensemble machine learning framework for the prediction of somatic mutations in cancer." BMC medical genomics 12 (2019): 1-14.
ARUP. "Exome Sequencing Symptom-Guided Analysis." ARUP Laboratories, 2013 [retrieved on Oct. 1, 2014]. Retrieved from the Internet: <URL:https://ltd.aruplab.com/Tests/Pub/2006332>, 2 pages.
Asan et al. "Comprehensive comparison of three commercial human whole-exome capture platforms." Genome biology 12 (2011): 1-12.
Ausubel et al. "Current Protocols in Molecular Biology—Table of Contents." New York, Greene Publishing Associates and Wiley-Interscience (1987): 1-8.
Bainbridge et al. "Whole exome capture in solution with 3 Gbp of data." Genome biology 11 (2010): 1-8.
Baird et al. "Developing recombinant antibodies for biomarker detection." Cancer Biomarkers 6.5-6 (2010): 271-279.
Bamshad et al. "Exome sequencing as a tool for Mendelian disease gene discovery." Nature Reviews Genetics 12.11 (2011): 745-755.
BCL2FASTQ Conversion User Guide, Manual [online], Illumina, 2013. Retrieved from the Internet: <URL:https://support.illumina.com/content/dam/illumina-support/documents/documentation/software_documentation/bcl2fastq/bcl2fastq_letterbooklet_15038058brpmi.pdf>, 30 pages.
Beck et al. "Profile of the circulating DNA in apparently healthy individuals." Clinical chemistry 55.4 (2009): 730-738.
Behjati et al. "Genome sequencing of normal cells reveals developmental lineages and mutational processes." Nature 513.7518 (2014): 422-425.
Benesova et al. "Mutation-based detection and monitoring of cell-free tumor DNA in peripheral blood of cancer patients." Analytical biochemistry 433.2 (2013): 227-234.
Bent et al. "Enriching pathogen transcripts from infected samples: a capture-based approach to enhanced host pathogen RNA sequencing." Analytical Biochemistry 438.1 (2013): 90-96.
Bentley et al. "Accurate whole human genome sequencing using reversible terminator chemistry." Nature 456.7218 (2008): 53-59.
Biesecker et al. "A genomic view of mosaicism and human disease." Nature Reviews Genetics 14.5 (2013): 307-320.
Bischoff et al. "Cell-free fetal DNA and intact fetal cells in maternal blood circulation: implications for first and second trimester non-invasive prenatal diagnosis." Human reproduction update 8.6 (2002): 493-500.
Blanco et al. "Highly efficient DNA synthesis by the phage phi 29 DNA polymerase. Symmetrical mode of DNA replication." The Journal of Biological Chemistry 264. 15 (1989): 8935-8940.
Blaschko, A. "The nerve distribution in the skin in their relation to the diseases of the skin." Presented at the VII Congress of the German Society of Dermatology, held at Wroclaw May 28-30 (1901): 1-60.
Blomquist et al. "Targeted RNA-sequencing with competitive multiplex-PCR amplicon libraries." PloS one 8.11 (2013): 1-14.
Boers et al. "High-throughput multilocus sequence typing: bringing molecular typing to the next level." PloS one 7.7 (2012): 1-8.
Bonadona et al. "Cancer risks associated with germline mutations in MLH1, MSH2, and MSH6 genes in Lynch syndrome." Jama 305.22 (2011): 2304-2310.
Boulesteix et al. "Evaluating microarray-based classifiers: an overview." Cancer informatics 6 (2008): 77-97.
Braslavsky et al. "Sequence information can be obtained from single DNA molecules." Proceedings of the National Academy of Sciences 100.7 (2003): 3960-3964.
Browne et al. "Increased promoter methylation in exfoliated breast epithelial cells in women with a previous breast biopsy." Epigenetics 6.12 (2011): 1425-1435.
Brunstein, J. "In-depth coverage: some useful NGS terms." Medical Laboratory Observer (MLO) 46.11 (2014): 1-5.
Bryzgunova et al. "Isolation and comparative study of cell-free nucleic acids from human urine." Annals of the New York Academy of Sciences 1075.1 (2006): 334-340.
Burrell et al. "The causes and consequences of genetic heterogeneity in cancer evolution." Nature 501.7467 (2013): 338-345.
Carlson et al. "Decoding cell lineage from acquired mutations using arbitrary deep sequencing." Nature methods 9.1 (2012): 78-80.
Chan et al. "Cancer genome scanning in plasma: detection of tumor-associated copy number aberrations, single-nucleotide variants, and tumoral heterogeneity by massively parallel sequencing." Clinical chemistry 59.1 (2013): 211-224.

(56) References Cited

OTHER PUBLICATIONS

Chang et al. "Role of bacteria in oncogenesis." Clinical microbiology reviews 23.4 (2010): 837-857.
Chapman et al. "Initial genome sequencing and analysis of multiple myeloma." Nature 471.7339 (2011): 467-472.
Chen et al. "A comprehensive, highly accurate genomics platform for precision immunotherapy: Simultaneously characterize tumors and the TME from a single FFPE sample." Personalis (2019): 1-1.
Chiu et al. "Cell-free DNA fragmentomics: the new 'Omics' on the block." Clinical chemistry 66.12 (2020): 1480-1484.
Chiu et al. "Effects of blood-processing protocols on fetal and total DNA quantification in maternal plasma." Clinical chemistry 47.9 (2001): 1607-1613.
Choi et al. "Genetic diagnosis by whole exome capture and massively parallel DNA sequencing." Proceedings of the National Academy of Sciences 106.45 (2009): 19096-19101.
Chu et al. "Statistical model for whole genome sequencing and its application to minimally invasive diagnosis of fetal genetic disease." Bioinformatics 25.10 (2009): 1244-1250.
Clark et al. "Performance comparison of exome DNA sequencing technologies." Nature biotechnology 29.10 (2011): 908-914.
Colella et al. "QuantiSNP: an Objective Bayes Hidden-Markov Model to detect and accurately map copy number variation using SNP genotyping data." Nucleic acids research 35.6 (2007): 2013-2025.
Craig et al. "Identification of genetic variants using bar-coded multiplexed sequencing." Nature methods 5.10 (2008): 887-893.
Cronn et al. "Multiplex sequencing of plant chloroplast genomes using Solexa sequencing-by-synthesis technology." Nucleic acids research 36.19 (2008): 1-11.
Cruz et al. "Applications of machine learning in cancer prediction and prognosis." Cancer informatics 2 (2006): 59-77.
Damani et al. "Characterization of circulating endothelial cells in acute myocardial infarction." Science translational medicine 4.126 (2012): 1-20.
Danovi, S. "A sequencing revolution in cancer." Milestones, Milestone 6, Nature, (2021): 1-1.
Davies et al. "Indications for hematopoietic cell transplantation in acute leukemia." Biology of Blood and Marrow Transplantation 14.1 (2008): 154-164.
Baez-Ortega. "Command-line manipulation of sequence files." In: In Silico, Sep. 22, 2018, [online] [retrieved on Oct. 23, 2025 (Oct. 23, 2025)] Retrieved from the Internet<URL:https://baezortega.github.io/2018/09/22/command-line-manipulation-sequence-files, 3 pages.
International Search Report and Written Opinion issued on Nov. 3, 2025 in corresponding PCT patent application No. PCT/US2025/035531, 9 pages.
Wan et al. "Transformiations for the compression of FASTQ quality scores of next-generation sequencing data." In: Bioinformatics. Mar. 1, 2012;28(5):628-35, [online] [retrieved on Oct. 23, 2025 (Oct. 23, 2025)] Retrieved from the Internet<URL: https://pubmed.ncbi.nlm.nih. gov/22171329, 8 pages.
Zhang et al. "Light-weight reference-based compression of FASTQ data." In: BMC Bioinformatics (2015) 16: 188, Jun. 9, 2015, [online] [retrieved on Oct. 23, 2025 (Oct. 23, 2025)] Retrieved from the Internet<URL: https://bmcbioinformatics.biomedcentral.com/articles/10.1186/s 12859-015-0628-7, 8 pages.
Human Genome Overview GRCh37.p13, Datasheet [online], Genome Reference Consortium, 2013 [retrieved on Sep. 12, 2022]. Retrieved from the Internet: <URL:https://www.ncbi.nlm.nih.gov/grc/human>, 2 pages.
Human Genome Overview GRCh38.p12, Datasheet [online], Genome Reference Consortium, 2017 [retrieved on Sep. 12, 2022]. Retrieved from the Internet: <URL:https://www.ncbi.nlm.nih.gov/assembly/GCF_000001405.38/>, 4 pages.
Illumina. "AmpliSeq for Illumina." Illumina, 2020. Retrieved from the Internet: <URL:https://web.archive.org/web/20201021103737/https://www.illumina.com/products/by-brand/ampliseq/custom-panels.html>, 3 pages.
Illumina. "Coverage Depth Recommendations: Learn how to estimate the depth of sequencing coverage needed for your research." Science and Education, Illumina, 2025. Retrieved from the Internet: <URL:https://www.illumina.com/science/technology/next-generation-sequencing/plan-experiments/coverage.html>, 3 pages.
Illumina. "Estimating sequencing coverage: Before starting a sequencing experiment, you should know the depth of sequencing you want to achieve. This technical note helps you estimate that coverage." Technical Note: Sequencing [online], Illumina, 2014. Retrieved from the Internet: <URL:https://www.illumina.com/documents/products/technotes/technote_coverage_calculation.pdf>, 2 pages.
Illumina. "Interpreting Infinium Assay Data for Whole-Genome Structural Variation." Technical Note: DNA Analysis [online], Illumina, 2010. Retrieved from the Internet: <URL:https://www.illumina.com/Documents/products/technotes/technote_cytoanalysis.pdf>, 8 pages.
Illumina. "Sequencing Coverage Calculation Methods for Human Whole-Genome Sequencing: An overview of Illumina coverage calculation methods using BaseSpace or third party analysis tools." Technical Note: Informatics [online], Illumina, 2014. Retrieved from the Internet: <URL:https://www.illumina.com/content/dam/illumina-marketing/documents/products/technotes/hiseq-x-30x-coverage-technical-note-770-2014-042.pdf>, 2 pages.
Ishii et al. "Optimization of annealing temperature to reduce bias caused by a primer mismatch in multitemplate PCR." Applied and environmental microbiology 67.8 (2001): 3753-3755.
Ito et al. "Cancer neoantigens: a promising source of immunogens for cancer immunotherapy." J Clin Cell Immunol 6.322 (2015): 1-7.
Jang et al. "Tumor mutation burden, immune checkpoint crosstalk and radiosensitivity in single-cell RNA sequencing data of breast cancer." Radiotherapy and Oncology 142 (2020): 202-209.
Jenjaroenpun et al. "Characterization of RNA in exosomes secreted by human breast cancer cell lines using next-generation sequencing." PeerJ 1 (2013): 1-24.
Jiang et al. "Plasma DNA end-motif profiling as a fragmentomic marker in cancer, pregnancy, and transplantation." Cancer Discovery 10.5 (2020): 664-673.
Jung et al. "Cell-free DNA in the blood as a solid tumor biomarker a critical appraisal of the literature." Clinica chimica acta 411.21-22 (2010): 1611-1624.
Kalatskaya et al. "ISOWN: accurate somatic mutation identification in the absence of normal tissue controls." Genome medicine 9 (2017): 1-18.
Kaper et al. "Parallel preparation of targeted resequencing libraries from 480 genomic regions using multiplex PCR on the Access Array system." Cancer Research 70.8 (2010): 1164.
Karam et al. "Apoptosis in carcinogenesis and chemotherapy." Netherlands: Springer (2009): 1-18.
Karolchik et al. "The UCSC Table Browser data retrieval tool." Nucleic acids research 32 (2004): D493-D496.
Khurana et al. "Integrative annotation of variants from 1092 humans: application to cancer genomics." Science 342.6154 (2013): 1-11.
Khurana et al. "Integrative annotation of variants from 1092 humans: application to cancer genomics." Supplementary Materials. Science 342.6154 (2013): 1-97.
Kiialainen et al. "Performance of microarray and liquid based capture methods for target enrichment for massively parallel sequencing and SNP discovery." PLoS One 6.2 (2011): 1-10.
Kinde et al. "Detection and quantification of rare mutations with massively parallel sequencing." Proceedings of the National Academy of Sciences 108.23 (2011): 9530-9535.
Koboldt et al. "VarScan: variant detection in massively parallel sequencing of individual and pooled samples." Bioinformatics 25.17 (2009): 2283-2285.
Kokawa et al. "Apoptosis in the human uterine endometrium during the menstrual cycle." The Journal of Clinical Endocrinology & Metabolism 81.11 (1996): 4144-4147.
Koren et al. "Differential relationship of DNA replication timing to different forms of human mutation and variation." The American Journal of Human Genetics 91.6 (2012): 1033-1040.
Kosuri et al. "Large-scale de novo DNA synthesis: technologies and applications." Nature methods 11.5 (2014): 499-507.

(56) References Cited

OTHER PUBLICATIONS

Kothari et al. "Emerging technologies for rapid identification of bloodstream pathogens." Clinical Infectious Diseases 59.2 (2014): 272-278.
Krumm et al. "Copy number variation detection and genotyping from exome sequence data." Genome research 22.8 (2012): 1525-1532.
Kuchler et al. "Buccal cells DNA extraction to obtain high quality human genomic DNA suitable for polymorphism genotyping by PCR-RFLP and Real-Time PCR." Journal of Applied Oral Science 20 (2012): 467-471.
Laktionov et al. "Cell-surface-bound nucleic acids: Free and cell-surface-bound nucleic acids in blood of healthy donors and breast cancer patients." Ann. NY Acad. Sci 1022 (2004): 221-227.
Lam et al. "Performance comparison of whole-genome sequencing platforms." Nature biotechnology 30.1 (2012): 78-82.
Lam et al. "Time course of early and late changes in plasma DNA in trauma patients." Clinical Chemistry 49.8 (2003): 1286-1291.
Larson et al. "SomaticSniper: identification of somatic point mutations in whole genome sequencing data." Bioinformatics 28.3 (2012): 311-317.
Lathe, R. "Synthetic oligonucleotide probes deduced from amino acid sequence data: theoretical and practical considerations." Journal of Molecular Biology 183.1 (1985): 1-14.
Leamon et al. "A massively parallel PicoTiterPlate based platform for discrete picoliter-scale polymerase chain reactions." Electrophoresis 24.21 (2003): 3769-3777.
Leary et al. "Detection of chromosomal alterations in the circulation of cancer patients with whole-genome sequencing." Science translational medicine 4.162 (2012): 1-21.
Leary et al. "Development of personalized tumor biomarkers using massively parallel sequencing." Science translational medicine 2.20 (2010): 1-15.
Lee et al. "Performance evaluation method for read mapping tool in clinical panel sequencing." Genes & genomics 40 (2018): 189-197.
Lee et al. "Simultaneous profiling of chromatin accessibility and methylation on human cell lines with nanopore sequencing." Nature methods 17.12 (2020): 1191-1199.
Lee et al. "The mutation spectrum revealed by paired genome sequences from a lung cancer patient." Nature 465.7297 (2010): 473-477.
Levin et al. "Targeted next-generation sequencing of a cancer transcriptome enhances detection of sequence variants and novel fusion transcripts." Genome biology 10 (2009): 1-8.
Ley et al. "DNA sequencing of a cytogenetically normal acute myeloid leukaemia genome." Nature 456.7218 (2008): 66-72.
Li et al. "Novel computational methods for increasing PCR primer design effectiveness in directed sequencing." BMC bioinformatics 9 (2008): 1-12.
Li et al. "The Sequence Alignment/MAP format and SAMtools." Bioinformatics 25.16 (2009): 2078-2079.
Liao et al. "Targeted massively parallel sequencing of maternal plasma DNA permits efficient and unbiased detection of fetal alleles." Clinical chemistry 57.1 (2011): 92-101.
Liu et al. "Computational approaches for characterizing the tumor immune microenvironment." Immunology 158.2 (2019): 70-84.
Liu et al. "Integrative molecular and clinical modeling of clinical outcomes to PD1 blockade in patients with metastatic melanoma." Nature medicine 25.12 (2019): 1916-1927.
Liu et al. "Placental mosaicism for trisomy 13: a challenge in providing the cell-free fetal DNA testing." Journal of assisted reproduction and genetics 31 (2014): 589-594.
Lizardi et al. "Mutation detection and single-molecule counting using isothermal rolling-circle amplification." Nature genetics 19.3 (1998): 225-232.
Lo et al. "Presence of fetal DNA in maternal plasma and serum." The lancet 350.9076 (1997): 485-487.
Lo et al. "Rapid clearance of fetal DNA from maternal plasma." The American Journal of Human Genetics 64.1 (1999): 218-224.
Lou et al. "High-throughput DNA sequencing errors are reduced by orders of magnitude using circle sequencing." Proceedings of the National Academy of Sciences 110.49 (2013): 19872-19877.
Lu et al. "A synthetic biology approach identifies the mammalian UPR RNA ligase RtcB." Molecular cell 55.5 (2014): 758-770.
Lu et al. "Cancer immunotherapy targeting neoantigens." Seminars in immunology 28.1 (2016): 22-27.
Lysov et al. "Efficiency of sequencing by hybridization on oligonucleotide matrix supplemented by measurement of the distance between DNA segments." DNA Sequence 6.2 (1996): 65-73.
Madeleine et al. "Comprehensive analysis of HLA-A, HLA-B, HLA-C, HLA-DRB1, and HLA-DQB1 loci and squamous cell cervical cancer risk." Cancer research 68.9 (2008): 3532-3539.
Maluf et al. "The urine microRNA profile may help monitor post-transplant renal graft function." Kidney international 85.2 (2014): 439-449.
Mamanova et al. "Target-enrichment strategies for next-generation sequencing." Nature methods 7.2 (2010): 111-118.
Marguerat et al. "RNA-seq: from technology to biology." Cellular and molecular life sciences 67 (2010): 569-579.
Margulies et al. "Genome sequencing in microfabricated high-density picolitre reactors." Nature 437.7057 (2005): 376-380.
Market et al. "V(D)J recombination and the evolution of the adaptive immune system." PLoS biology 1.1 (2003): 024-027.
Marsh, S. "Pyrosequencing applications." Methods Mol Biol. (2007): 15-24.
Marusyk et al. "Tumor heterogeneity: causes and consequences." Biochimica et Biophysica Acta (BBA)—Reviews on Cancer 1805.1 (2010): 105-117.
Masuzaki et al. "Detection of cell free placental DNA in maternal plasma: direct evidence from three cases of confined placental mosaicism." Journal of medical genetics 41.4 (2004): 289-292.
Mcbride et al. "Use of cancer-specific genomic rearrangements to quantify disease burden in plasma from patients with solid tumors." Genes, Chromosomes and Cancer 49.11 (2010): 1062-1069.
Mercer et al. "Targeted sequencing for gene discovery and quantification using RNA CaptureSeq." Nature protocols 9.5 (2014): 989-1009.
Mertes et al. "Targeted enrichment of genomic DNA regions for next-generation sequencing." Briefings in functional genomics 10.6 (2011): 374-386.
Meyerson et al. "Advances in understanding cancer genomes through second-generation sequencing." Nature Reviews Genetics 11.10 (2010): 685-696.
Michaelson et al. "Whole-genome sequencing in autism identifies hot spots for de novo germline mutation." Cell 151.7 (2012): 1431-1442.
Miller et al. "Basic concepts of microarrays and potential applications in clinical microbiology." Clinical microbiology reviews 22.4 (2009): 611-633.
Misawa et al. "Significance of chromosomal alterations and mutations of the N-RAS and TP53 genes in relation to leukemogenesis of acute myeloid leukemia." Leukemia research 22.7 (1998): 631-637.
Mitra et al. "In situ localized amplification and contact replication of many individual DNA molecules." Nucleic Acids Research 27.24 (1999): e34-e39.
Moore et al. "Direct screening of blood by PCR and pyrosequencing for a 16S rRNA gene target from emergency department and intensive care unit patients being evaluated for bloodstream infection." Journal of clinical microbiology 54.1 (2016): 99-105.
Moss et al. "Comprehensive human cell-type methylation atlas reveals origins of circulating cell-free DNA in health and disease." Nature communications 9.1 (2018): 1-12.
Moudrianakis et al. "Base sequence determination in nucleic acids with the electron microscope, III. Chemistry and microscopy of guanine-labeled DNA." Proceedings of the National Academy of Sciences 53.3 (1965): 564-571.
Muniappan et al. "The DNA polymerase β replication error spectrum in the adenomatous polyposis coli gene contains human colon tumor mutational hotspots." Cancer research 62.11 (2002): 3271-3275.

(56) References Cited

OTHER PUBLICATIONS

Murray et al. "Improved double-stranded DNA sequencing using the linear polymerase chain reaction." Nucleic Acids Research 17.21 (1989): 8889-8889.
Naxerova et al. "Hypermutable DNA chronicles the evolution of human colon cancer." Proceedings of the National Academy of Sciences 111.18 (2014): E1889-E1898.
Naxerova et al. "Using tumour phylogenetics to identify the roots of metastasis in humans." Nature reviews Clinical oncology 12.5 (2015): 258-272.
Newman et al. "An ultrasensitive method for quantitating circulating tumor DNA with broad patient coverage." Nature medicine 20.5 (2014): 548-554.
Newman et al. "An ultrasensitive method for quantitating circulating tumor DNA with broad patient coverage." Supplementary Tables. Nature medicine 20.5 (2014): 1-151.
Newman et al. "Integrated digital error suppression for improved detection of circulating tumor DNA." Nature biotechnology 34.5 (2016): 547-555.
Ng et al. "Exome sequencing identifies the cause of a mendelian disorder." Nature genetics 42.1 (2010): 30-35.
Ng et al. "Targeted capture and massively parallel sequencing of 12 human exomes." Nature 461.7261 (2009): 272-276.
Novocraft Technologies SDN BHD, Company Information [online], Novocraft Technologies Sdn Bhd, 2014. Retrieved from the Internet: <URL:http://www.novocraft.com/>, 2 pages.
Nucleosome Position by MNase-seq from ENCODE-Stanford-BYU, Datasheet [online], 2011-2012. Retrieved from the Internet: <URL:http://hgdownload.cse.ucsc.edu/goldenPath/hg19/encodeDCC/wgEncodeSydhNsome/>, 2 pages.
Ochman et al. "Genetic applications of an inverse polymerase chain reaction." Genetics 120.3 (1988): 621-623.
Oesper et al. "Quantifying tumor heterogeneity in whole-genome and whole-exome sequencing data." Bioinformatics 30.24 (2014): 3532-3540.
Okosun et al. "Integrated genomic analysis identifies recurrent mutations and evolution patterns driving the initiation and progression of follicular lymphoma." Nature genetics 46.2 (2014): 176-181.
Okosun et al. "Whole Genome Sequencing in Sequential Biopsies Reveals the Genetic Evolution of Follicular Lymphoma to Transformed Follicular Lymphoma." (2012): 1-3.
Ozsolak et al. "Direct RNA sequencing." Nature 461.7265 (2009): 814-818.
Park, A. "Scientists Devise a Blood Test to Predict Heart Attack." Time Magazine. (2012): 1-2.
Pasaniuc et al. "Extremely low-coverage sequencing and imputation increases power for genome-wide association studies." Nature genetics 44.6 (2012): 631-635.
Pathak et al. "Circulating cell-free DNA in plasma/serum of lung cancer patients as a potential screening and prognostic tool." Clinical chemistry 52.10 (2006): 1833-1842.
Pierce et al. "Linear-after-the-exponential polymerase chain reaction and allied technologies: Real-time detection strategies for rapid, reliable diagnosis from single cells." Single Cell Diagnostics: Methods and Protocols (2007): 65-85.
Podlaha et al. "Evolution of the cancer genome." Trends in Genetics 28.4 (2012): 155-163.
Pritchard et al. "ColoSeq provides comprehensive lynch and polyposis syndrome mutational analysis using massively parallel sequencing." The Journal of Molecular Diagnostics 14.4 (2012): 357-366.
Punnoose et al. "Molecular biomarker analyses using circulating tumor cells." PloS one 5.9 (2010): 1-12.
Pyke et al. "Precision neoantigen discovery using large-scale immunopeptidomes and composite modeling of MHC peptide presentation." Molecular & Cellular Proteomics 20 (2021): 1-19.
Pyke et al. "Precision neoantigen discovery using large-scale immunopeptidomes and composite modeling of MHC peptide presentation." Supplementary Materials, bioRxiv (2021): 1-37.
Qiagen. "QIAamp DNA Mini Kit and QIAamp DNA Blood Mini Kit Handbook." Datasheet [online], QIAGEN, 2003. Retrieved from the Internet: <URL:https://depts.washington.edu/kellylab/wordpress/wp-content/uploads/2019/03/QIAGEN_protocol.pdf>, 68 pages.

* cited by examiner

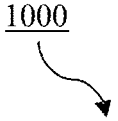
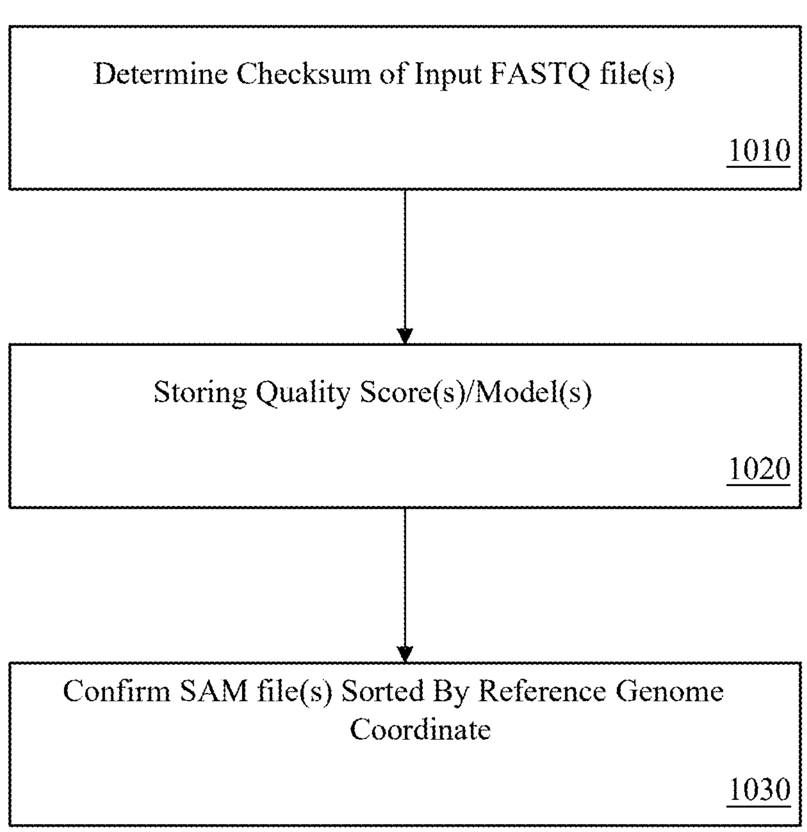
Fig. 2

```
#:SENTIEON_QCAL_TABLE.V1:5
#:SENTIEON_QCAL_TABLE:2:17;
#:SENTIEON_QCAL_TABLE:Arguments:Recalibration argument collection values used in this run
Argument        Value
binary_tag_name null
covariate       ReadGroupCovariate,QualityScoreCovariate,ContextCovariate,CycleCovariate
default_platform        null
deletions_default_quality       45
force_platform  null
indels_context_size     3
insertions_default_quality      45
low_quality_tail        2
maximum_cycle_value     500
mismatches_context_size 2
mismatches_default_quality      -1
no_standard_covs        false
quantizing_levels       16
recalibration_report    null
run_without_dbsnp       false
solid_nocall_strategy   THROW_EXCEPTION
solid_recal_mode        SET_Q_ZERO

#:SENTIEON_QCAL_TABLE:3:94
#:SENTIEON_QCAL_TABLE:Quantized:Quality quantization map
QualityScore    Count   QuantizedScore
0       0       93
1       0       93
2       0       93
3       0       93
4       0       93
5       0       93
6       0       93
7       0       93
8       0       93
9       0       93
10      207741314       10
11      0       93
12      0       93
13      0       93
14      0       93
15      0       93
16      0       93
17      0       93
18      0       93
19      0       93
20      0       93
21      0       93
22      0       93
23      497887989       23
```

Fig. 4

```
#:SENTIEON_QCAL_TABLE:6:12
#:SENTIEON_QCAL_TABLE:RecalTable0:
ReadGroup       EventType       EmpiricalQuality        EstimatedQReported        Observations      Errors
H7CCGDSX3.4     M        26.0000 27.6695 2884746887      6802866.57
H7CCGDSX3.4     I        43.0000 45.0000 2884746887      137594.87
H7CCGDSX3.4     D        41.0000 45.0000 2884746887      248517.04
H7CCGDSX3.3     M        26.0000 27.5893 2902648950      7450654.21
H7CCGDSX3.3     I        43.0000 45.0000 2902648950      138882.98
H7CCGDSX3.3     D        41.0000 45.0000 2902648950      250761.73
H7CCGDSX3.2     M        26.0000 27.3372 2798995200      7675228.26
H7CCGDSX3.2     I        43.0000 45.0000 2798995200      131942.89
H7CCGDSX3.2     D        41.0000 45.0000 2798995200      239449.69
H7CCGDSX3.1     M        26.0000 27.5913 2739767180      6787058.13
H7CCGDSX3.1     I        43.0000 45.0000 2739767180      130112.31
H7CCGDSX3.1     D        41.0000 45.0000 2739767180      235571.05
```

```
#:SENTIEON_QCAL_TABLE:8:6576
#:SENTIEON_QCAL_TABLE:RecalTable2:
ReadGroup       QualityScore    CovariateValue    CovariateName    EventType     EmpiricalQuality     Observations      Errors
H7CCGDSX3.4     11       AA      ContextM          9.00     5698047 752600.64
H7CCGDSX3.4     11       CA      ContextM          7.00     3379959 701635.72
H7CCGDSX3.4     11       GA      ContextM          8.00     2474599 430039.51
H7CCGDSX3.4     11       TA      ContextM          6.00     3194288 769968.15
H7CCGDSX3.4     11       AC      ContextM          9.00     2068042 253381.02
H7CCGDSX3.4     11       CC      ContextM          11.00    2034524 152769.17
H7CCGDSX3.4     11       GC      ContextM          13.00    1617139 79922.90
H7CCGDSX3.4     11       TC      ContextM          12.00    2418782 169759.25
H7CCGDSX3.4     11       AG      ContextM          13.00    4013731 219443.52
H7CCGDSX3.4     11       CG      ContextM          5.00     701512  229257.48
H7CCGDSX3.4     11       GG      ContextM          12.00    2478915 172932.08
H7CCGDSX3.4     11       TG      ContextM          12.00    3364522 220769.44
H7CCGDSX3.4     11       AT      ContextM          11.00    5027843 427978.25
H7CCGDSX3.4     11       CT      ContextM          16.00    4186709 97690.26
H7CCGDSX3.4     11       GT      ContextM          11.00    3130206 278265.49
H7CCGDSX3.4     11       TT      ContextM          12.00    5197579 322225.19
H7CCGDSX3.4     25       AA      ContextM          22.00    12695296        77408.98
H7CCGDSX3.4     25       CA      ContextM          20.00    6737309 66170.71
H7CCGDSX3.4     25       GA      ContextM          21.00    5684873 44024.24
```

Fig. 4
(cont'd)

SYSTEM AND METHOD FOR MANAGEMENT OF COMPRESSED SEQUENCING FILES

CROSS-REFERENCE TO RELATED APPLICATIONS

This application claims priority to U.S. Provisional Application No. 63/665,079, which was filed Jun. 27, 2024. The disclosure of the patent application is herein incorporated by reference in its entirety and for all purposes.

FIELD

The present application generally relates to systems and methods for storing genetic sequencing data and, more specifically, but not exclusively, for management of compressed filetypes storing biological sequences.

BACKGROUND

Next generation sequencing data presents a number of challenges with respect to storing and analyzing sequencing data, primarily due to the size of such datasets. For example, for products that can provide an advanced, personalized, tumor-informed liquid biopsy assay to detect molecular residual disease and cancer recurrence—such as NeXT Personal® from Personalis in Fremont, CA—approximately 2.3 billion sequencing reads are used in order to gain insights about a patient's tumor, enabling a custom assay to quantify minimal residual disease as the patient undergoes treatment. Altogether, the uncompressed "raw" sequencing data used for the initial bioinformatics analysis of a single patient represents nearly 850 gigabytes of information.

Of particular importance is the need to efficiently store sequencing data in a manner that enables rapid generation and reconstruction of data in various formats on the fly. Unfortunately, conventional solutions cannot provide this solution.

For example, FASTQ format is a text-based format for storing both a biological sequence (usually nucleotide sequence) and its corresponding quality scores. Both the sequence letter and quality score are each encoded with a single ASCII character for brevity. The FASTQ file format is the industry standard for storing un-aligned sequencing data, i.e., the "raw" sequencing data which represents base calls and associated quality scores as determined by the DNA/RNA sequencer and its associated analysis software. FASTQ files are typically used as the starting point of any sequencing data bioinformatics analysis workflow.

But FASTQ files typically contain up to millions of entries and can be several megabytes or gigabytes in size, which can make them too large to open and analyze by conventional text editors. Generally, conventional systems only use FASTQ files as input for tools that perform downstream analysis, such as alignment to a reference assembly.

The Sequence Alignment Map (SAM) file format is the industry standard for storing reference-based aligned sequence data in a text-based format. SAM files may be encoded in plaintext (SAM) or in a binary version of SAM (i.e., a Binary Alignment Map (BAM)), which uses block-level compression to compress sequence data with respect to the similarity/difference of the associated reference genome (i.e., Compressed Reference-Oriented Alignment Map (CRAM)). As used herein, for ease of discussion only, both BAM and CRAM encodings will be referred to as "compressed SAM" files.

It is often necessary to repeat bioinformatics analysis, starting from either un-aligned (FASTQ-formatted) or aligned (SAM-formatted) sequencing data. But due to the sheer size of files and the amount of computation necessary to repeat alignment, it is ideal to only store sequencing data in aligned SAM format, and regenerate FASTQ files if/when necessary. But conventional systems may not guarantee regeneration of FASTQ files that are substantively identical to the original FASTQ file.

In view of the foregoing, a need exists for an improved file management system and method for converting compressed SAM files back into raw FASTQ files in an effort to overcome the aforementioned obstacles and deficiencies of conventional file management systems.

BRIEF DESCRIPTION OF THE DRAWINGS

The novel features of the disclosed systems and methods are set forth with particularity in the appended claims. A better understanding of the features and advantages of the present systems and methods will be obtained by reference to the following detailed description that sets forth illustrative embodiments, in which the principles of the invention are used, and the accompanying drawings (also "Fig.", "FIG.", "Figure", "Figures", "Figs.", and "FIGs." herein) of which:

FIG. 2 shows a flow diagram illustrating one embodiment of the preprocessing steps of an input FASTQ file and a compressed SAM file of FIG. 1.

FIG. 4 shows an exemplary screenshot illustrating one embodiment of a BQSR model.

Figure 1:
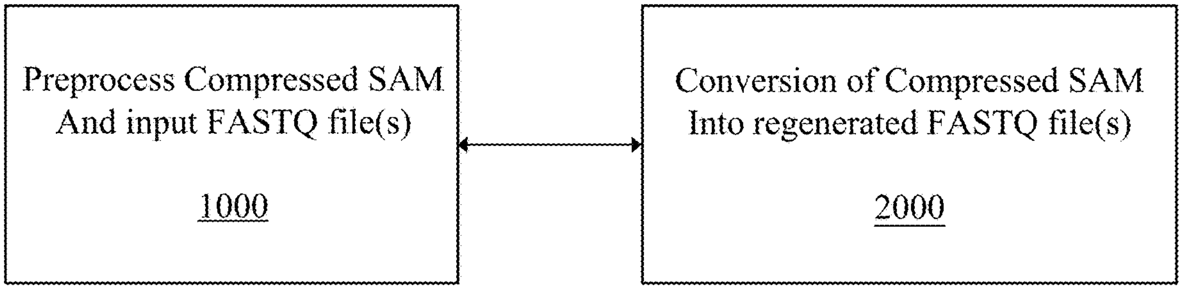
FIG. 1 shows a top level block diagram illustrating one embodiment of data flow for managing a compressed sequencing file.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION

The description is presented to enable one of ordinary skill in the art to make and use the systems and methods and is provided in the context of a patent application and its requirements. The section headings used herein are for organization purposes only and are not to be construed as limiting the subject matter described. While various embodiments of the systems and methods of the present disclosure have been shown and described herein, it will be obvious to those skilled in the art that such embodiments are provided by way of example only. Numerous variations, changes, and substitutions may occur to those skilled in the art without departing from the invention(s). It should be understood that various alternatives to the embodiments of the systems and methods described herein may be employed in practicing any one of the systems and methods set forth herein.

All patents, published patent applications, other publications, and sequences from GenBank, and other databases referred to herein are incorporated by reference in their entirety with respect to the related technology.

I. Definitions

Unless defined otherwise, technical, and scientific terms used herein have the same meaning as commonly understood by one of ordinary skill in the art to which the present disclosure belongs. For purposes of the present disclosure, the following terms are defined below. The definitions provided are intended to apply to a given term, as well as other derivative linguistic re-phrasings and grammatical equivalents of the term.

As used herein, the term "compressed SAM" refers to both Binary Alignment Map (BAM) files and Compressed Reference-Oriented Alignment Map (CRAM) files.

As used herein, the singular forms "a," "an", and "the" include plural referents unless the context clearly dictates otherwise. Thus, for example, reference to "an antigen" includes mixtures of antigens; reference to "a pharmaceutically acceptable carrier" includes mixtures of two or more such carriers, and the like. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A (alone)", and "B (alone)".

As used herein, the term "about" a value (or parameter) refers to ±10% of a stated value. When referring to a range of values (or parameters), the term "about" refers to +10% of the upper limit and −10% of the lower limit of a stated range of values. When a range of values is provided, it is to be understood that each intervening value between the upper and lower limit of that range, and any other stated or intervening value in that stated range, is encompassed within the scope of the present disclosure. Where the stated range includes upper and/or lower limits, ranges excluding either of those included limits are also included in the present disclosure.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

II. Overview

The present disclosure is directed to systems and methods for management of storing and analyzing genetic sequencing data. In some embodiments disclosed herein, a method for converting a compressed SAM file back into a raw FASTQ file, wherein the information of the raw FASTQ file is substantively identical to that which was stored in the original FASTQ file from which the compressed SAM file is based is provided. The method advantageously enables storage of the smaller compressed SAM files for reliable, efficient reconstruction of the original FASTQ file when needed.

For example, in a typical workflow, sequencers can use various technology (e.g., cluster generation and sequencing by synthesis) to sequence millions or billions of clusters on a flow cell. For each cluster, base calls are made and stored for every cycle of sequencing by real-time-analysis software. When sequencing completes, the base calls are converted to sequence data, typically stored in a FASTQ file. The FASTQ file is a test file that contains the sequence data from the clusters that pass filters on a flow cell.

In some embodiments, each entry of the FASTQ file includes at least four line-separated fields per sequence: (1) sequence identifier; (2) sequence; (3) quality score identifier line; and (4) a quality score. Field 1 begins with a '@' character and is followed by a sequence identifier and an optional description (like a FASTA title line). Field 2 is the raw sequence letters. Field 3 begins with a '+' character and is optionally followed by the same sequence identifier (and any description) again. Field 4 encodes the quality values for the sequence in Field 2, and includes the same number of symbols as letters in the sequence.

The first field "Field 1" can be stored in two places: (1) The required SAM field QNAME stores the FASTQ sequence identifier; or (2) The optional description/comments is stored in the SAM format with a custom SAM tag.

The second field, "Field 2" can be stored in the SAM "SEQ" field.

The third field is typically assumed to be a "+". The fourth field can either stored in the SAM "QUAL" field, or if these scores have been recalibrated via BQSR, a custom SAM tag is used to preserve the original contents of the fourth field. Additionally and/or alternatively, the BQSR model can be saved, and an inversion of the BQSR model is run on the SAM QUAL field. This can potentially save more space but introduce error.

Additional information regarding FASTQ files, for example, can be found in the bcl2fastq Conversion User Guide, available at https://support.illumina.com/content/dam/illumina-support/documents/documentation/software_documentation/bcl2fastq/bcl2fastq_letterbooklet_15038058brpmi.pdf, the FASTQ format Wikipedia, available at https://en.wikipedia.org/wiki/FASTQ_format, and the Sequence Alignment/Map Format Specification, available at https://samtools.github.io/hts-specs/SAMv1.pdf, which articles are hereby incorporated by reference in their entirety for all purposes. This original FASTQ file is often large.

Alignment data for large numbers of aligned reads are often output as sequence alignment and map (SAM) or binary alignment and map (BAM) files. An aligner usually takes in raw sequence data in the form of a FASTQ file along with a reference genome to generate a new file containing the reads as well as the genomic location from which they originated. But due to the sheer size of files and the amount of computation necessary to repeat alignment, it is ideal to only store sequencing data in aligned SAM format, and regenerate FASTQ files if/when necessary.

In some embodiments, a method for converting a compressed SAM file back into a raw FASTQ file is shown in FIG. 1. The disclosed methods are applicable to plaintext SAM, BAM, and CRAM encodings, and particularly useful for compressed SAM files. By providing a reliable method to recreate/regenerate a FASTQ file and verify its integrity, it is not necessary to store the original input FASTQ file.

Instead, with the disclosed systems and methods, storing compressed SAM files are sufficient for preserving necessary sequencing data. As shown in FIG. 1, the method comprises at least two major subprocesses. Prior to any regeneration of a FASTQ file from a compressed SAM file, the method includes a preprocessing step 1000 of the compressed SAM file and the input FASTQ file on which the compressed SAM file is based. FIG. 1 also shows the process 2000 for regenerating a file that is substantively identical to the input FASTQ file based on the compressed SAM file created therefrom.

With reference to FIG. 2, the preprocessing step 1000 of the compressed SAM file and the input FASTQ file is shown in further detail. For example, once a compressed SAM file is generated from an input FASTQ file, the preprocessing step 1000 first determines a checksum—hereinafter referred to as FQSUM—of the input FASTQ file (process 1010), which is used for data integrity.

In some embodiments, when operating with tens of billions of base pairs of sequencing data, it is advantageous to remove redundant data wherever possible, primarily for the sake of resource/cost savings. For example, when operating at a scale where a computer's resources (e.g., memory/disk space) is easily overwhelmed, it can be advantageous to remove the original input FASTQ file once all information is stored in a CRAM file (which in fact has more information (alignment information), while using less disk space than the FASTQ). In other words, a file size of the CRAM file is much smaller than the original input FASTQ file it is based on. Therefore, the FQSUM can be calculated at any time before the original input FASTQ file is deleted.

The FQSUM is determined using an idempotent, commutative, and associative checksum algorithm. Stated in another way, for some set of one or more FASTQ records-A and B:

$$fqsum(\{A\}) = fqsum(fqsum(\{A\}))$$

and $$fqsum(\{A, B\}) = fqsum(\{B, A\})$$

and $$fqsum(\{fqsum(\{A, B\}), C\}) = fqsum(\{A, fqsum(\{B, C\})\})$$

Advantageously, the FQSUM can be used to verify data integrity without the need for sorting or re-ordering either the original input FASTQ files (or any intermediate output of the disclosed process). Compared to a conventional checksum, the FQSUM is advantageously order invariant. Since SAM files are typically stored in order of alignment (which reduces entropy and increases compression), converting directly from a SAM file to FASTQ, then running a checksum such as MD5 generally yields a different checksum than calculating the MD5 checksum on the original FASTQ input. Re-ordering the FASTQ output to resemble the input of the original FASTQ input is computationally prohibitive, as any such algorithm either requires: (1) a large amount of memory to run, generally equal to the amount of FASTQ data, or (2) require many iterations over the data and be very computationally slow. Since the order of the original FASTQ input is generally not meaningful (for example, pseudo-random), the FQSUM checksum advantageously ignores order and calculates the checksum on the set of reads (two sets being identical even if their elements appear in a different order). In some embodiments, the following pseudocode is used to determine the FQSUM:

```
fqsum_t fqsum(fq_t fastq_records) {
  fqsum_t fqsum_hash;
  for (record in fastq_records) {
      uint n = strlen(record.HEADER);
    for (uint i=0;i<n;i++)
        fqsum_hash->HEADER[i] = (fqsum_hash->HEADER[i] + record.HEADER[i]-32)%95;
    }
    assert(strlen(record.SEQ) == strlen(record.QUAL));
    n = strlen(record.SEQ);
    for (uint i=0; i<n;i++) {
        fqsum_hash->SEQ[i] = (fqsum_hash->SEQ[i] + record.SEQ[i]-33)%94;
        fqsum_hash->QUAL[i] = (fqsum_hash->QUAL[i] + record.QUAL[i]-33)%94;
    }
  }
  return fqsum_hash;
}
```

As shown in the pseudocode, the method to determine the FQSUM is invariant to the order of FASTQ records due to its commutative property. In other words, the FQSUM for the same set of FASTQ reads, either in a pseudo-random order output by sequencer software or in "sorted by alignment" order, advantageously are identical. Using the FQSUM for data integrity or verification is linear in time complexity and does not require sorting FASTQ files, which is typically impractical given the file sizes typically associated with conventional FASTQ files.

Turning back to FIG. 2, the preprocessing step 1000 of the compressed SAM file and the input FASTQ file then stores only the information necessary to construct original quality scores, even after the application of base quality score recalibration (BQSR) (process 1020). For example, a quality score can be a string of integers, equal in length to the sequence string, articulating the respective quality of each base call as it appears in the sequence string. If there are 100 bases in a read, there are 100 associated quality scores. Quality scores are generally represented on an integer scale of 0-91 (e.g., a Phred quality score). +33 is added and represented as ASCII characters with decimal representation 33 through 126, i.e., "!" is used to represent "0", and "~" is used to represent "91".

Base quality scores are typically done at sequencing imaging time—a relative confidence of each base call is made, with Phred scaled score 0-91. Once a sequencing run is completed, the base quality scores is typically "recalibrated" by accounting for the entire dataset of quality scores, to ensure they make sense. BQSR is therefore a process where machine learning is applied to model these errors empirically and adjust the quality scores accordingly. For example, for a given run, whenever two A nucleotides are called in a row, the next base called had a 1% higher rate of error. Thus, any base call that comes after AA in a read should have its quality score reduced by 1%. That is repeated over several different covariates (mainly sequence context and position in read, or cycle) in a way that is additive. The same base may have its quality score increased for one reason and decreased for another.

In some embodiments, the recalibrated base quality scores appear in the same format as the original quality scores—e.g., a Phred scaled score (0-91)+33 and represented as an ASCII character. In other words, it is difficult to distinguish between "original" and "recalibrated" quality scores just by looking at the string of scores. In some embodiments, this storage is done by either storing the quality score model or by directly storing the original quality scores in a reserved SAM "tag."

The BQSR model can be stored as a separate file, or within the SAM file "header", for example, using an optional tag (e.g., @CO tag). For directly storing the original quality scores in a reserved SAM tag, the original quality string can be stored using an optional alignment field (e.g., @XQ tag). An example of storing the original quality score directly includes: XQ:Z:,:,FFF,,FFFFF:F:FFF,:FFF:,FFFFF:FFFFFFFF:FFFFF:FF::FF:FF:F,FF,,F:F,FF,FF,:F:FFFF:F:F:F:F:F,FF,FF:F:F,F,FFFFF:FFFFFFFFFFF:FFFFFFFFFFF-FFFFFFFFFFFFFFFFFF Where "XQ" is the tag name, and "Z" indicates the data is a string.

The actual quality string is: ,:,FFF,,FFFFF:F:FFF,:FFF:,FFFFF:FFFFFFFF:FFFFF:FF::FF:FF:F,FF,,F:F,FF,FF,:F:F-FFF:F:F:F:F:F,FF,FF:F:F,F,FFFFF:FFFFFFFFFFF:FFFFF-FFFFFFFFFFFFFFFFFFFFFFFF Finally, at step 1030, the preprocessing step 1000 ensures that SAM records in the compressed SAM files are stored in a sorted order in order to reduce entropy and enable better compression of the compressed SAM file, as well as when compressing the FASTQ files generated by the present disclosure. In some embodiments, the SAM file can be sorted in a variety of methods to benefit the compression ratio. By way of example, two exemplary methods to sort the SAM file to ensure that entropy is reduced includes: (1) Sorting by reference genome coordinate(s); or (2) Sorting by sequence string.

In the context of the SAM specification, most bioinformatics tools expect a SAM file to be provided in sorted-by-reference-genome-coordinate order (method 1), and leverages the indexing mechanism available in SAM specification, which allows for quick retrieval of reads that fall within a provided reference genome coordinate.

In other embodiments, the SAM file is sorted by sequence string. Although less typical, similar reads, e.g., all reads that start with "AAA . . . " appear together in the file. But SAM does not provide any indexing mechanism for this and retrieve reads are slower if the file is stored in this manner.

Figure 3:
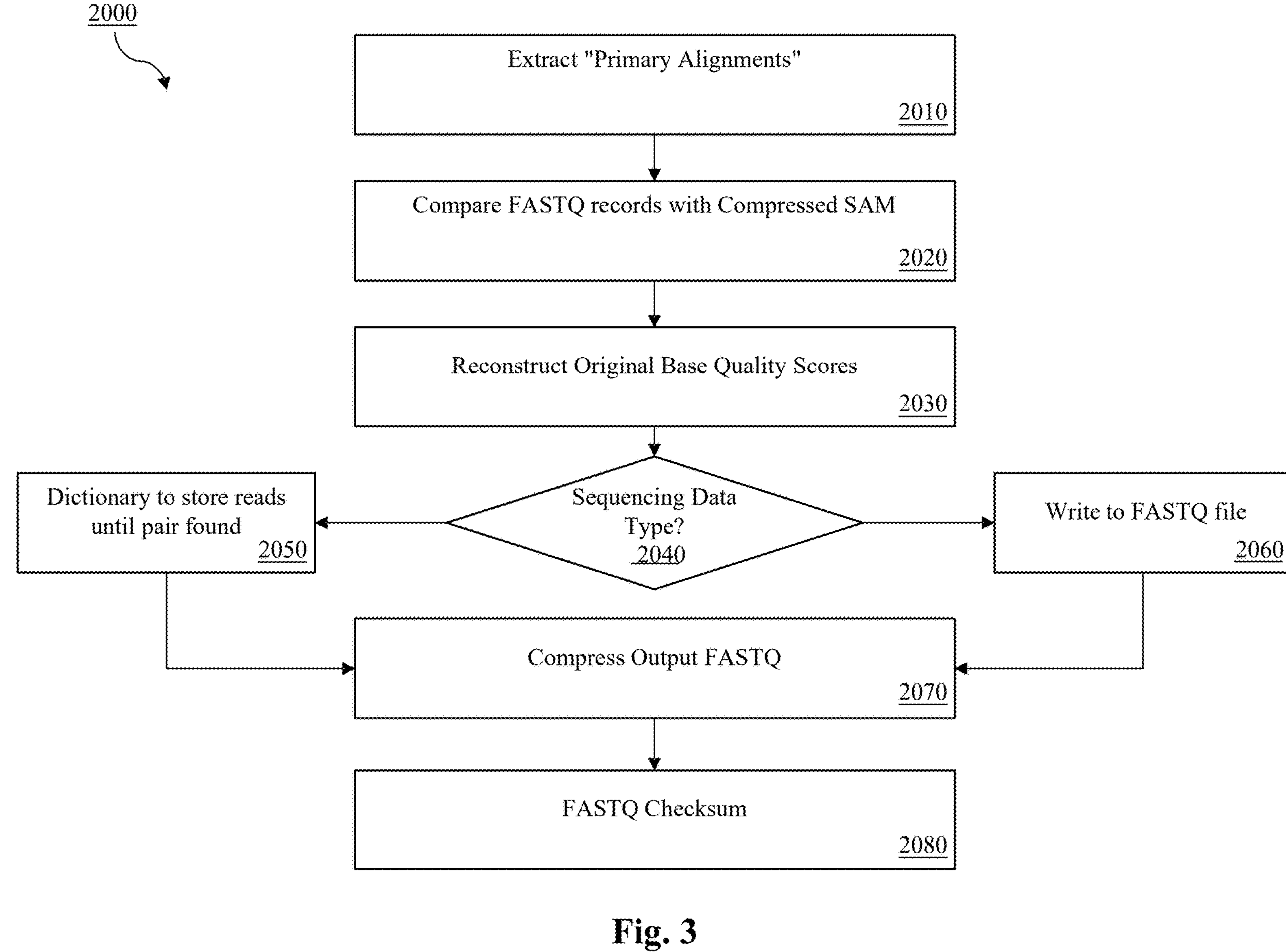
FIG. 3 shows a flow diagram illustrating one embodiment of the regeneration of a FASTQ file from a compressed SAM file of FIG. 1.
Figure 5:
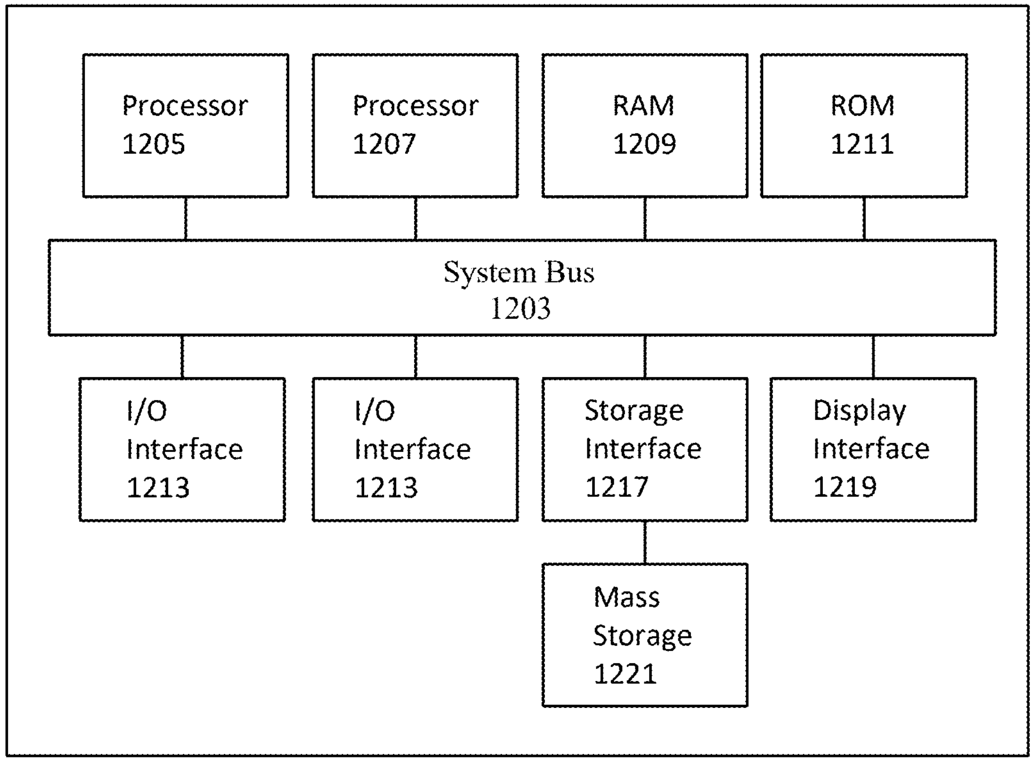
FIG. 5 shows an example computer, according to various embodiments.

Following the preprocessing steps 1000, the process 2000 for regenerating a file that is substantively identical to the input FASTQ file based on the compressed SAM file created therefrom is detailed in FIG. 3. With reference to FIG. 3, the process 2000 begins by extracting only "primary alignments" from the compressed SAM file to ensure that there is no duplication of records in the output FASTQ files.

By way of example, assume a sequencing read with ID "ABC". At the FASTQ level, the sequencing read IDs are unique with respect to each read or read-pair. If ABC only plausibly aligns to one part of the reference genome, then it will appear only once in the SAM file, and will be denotated as the "primary" alignment. There will be no secondary/supplementary alignment records for read "ABC".

If ABC potentially aligns to different parts of the reference genome, multiple instances of sequence read "ABC" may be present in the SAM file. This is because the aligner indicates "it could map to location X, or Y or Z". However, only one of these alignments is flagged to be "primary". The other alignments are denoted as secondary or supplementary.

Since "ABC" should not appear multiple times in the reconstructed FASTQ file (as it only appeared once in the input), the system only considers the primary alignment.

At step 2020, the system confirms whether all FASTQ records of the original input FASTQ file is stored in the compressed SAM file (via the FQSUM). In some embodiments, it may be advantageous to remove sequencing duplicates or off-target reads and store these sequencing duplicates and/or off-target reads in an "auxiliary" compressed SAM file. For example, off-target reads include sequencing reads that are not directed to the targeted portion of the sequencing assay. During exome sequencing, to target the subset of DNA encoding proteins, primers and/or capture probes are configured with at least a subset designed to capture the flanking regions of a coding region. Frequently, there is sequencing beyond the coding portion, resulting in at least a portion of the read being off target. Sequence reads are usually generated over the course of the sequencing reaction and are subsequently reviewed/processed once the experiment is complete. If it is desired to exclude certain reads from the primary SAM file that is used for bioinformatics analysis, such as sequencing duplicates and/or off-target reads, the system can store such reads in the "auxiliary" compressed SAM file to ensure that such reads can still be reconstructed in FASTQ format at a later time in the case that bioinformatics analysis on these reads is later desired. In some embodiments, the "auxiliary" SAM file is identical in structure and format to the primary SAM file.

Furthermore, due to the properties of FQSUM, the system can then determine if FQSUM(original_FASTQ)=FQSUM (FQSUM(CHIEF_SAM_FASTQ), FQSUM(AUX_SAM_FASTQ)) to segregate "undesirable" reads from the initial bioinformatics analysis on the input SAM file, while still maintaining the flexibility to reconstruct those reads down the road if desired.

At step 2030, the original base quality scores are reconstructed either by grabbing directly from the reserved SAM tag, or applying the inverse of the BQSR model.

The BQSR model can be calculated on a per-sample basis, and is generally stored as a text file, used as a "ruleset" for the BQSR process to recalibrate reads.

If recalibrated_qualities=bqsr (model, original_qualities), this process can be inverted by saving the BQSR model:

$$\text{original\_qualities}=\text{bqsr}^{-1}(\text{model},\text{recalibrated\_qualities})$$

An exemplary screenshot of an exemplary BQSR file is shown in FIG. 4.

If using paired-end sequencing data (decision 2040), a dictionary is used to store reads in memory until its "mate" is found (step 2050). In some embodiments, paired-end sequencing data is reflected in the presentation of data in FASTQ format. Typically, paired-end sequencing data where two reads are "mated" together and have the same sequence identifier is received via pairs of FASTQ files. For example, "read 1" of each read pair is in a "read 1" FASTQ file, and "read 2" of each read pair is in a "read 2" FASTQ file. Both reads of a read pair can be stored in the same SAM file—there is a "SAM flag" which indicates whether the read is read 1 or read 2.

The disclosed method parses through the SAM file. If read 1 appears first, the system stores read 1 in memory until read 2 is found, and vice versa. When both "read 1" and "read 2" of a certain sequence identifier are available, read 1 will be written to the "read 1" FASTQ file, and "read 2" will be written to the "read 2" FASTQ file.

Paired FASTQ files must have reads appear in the same order. If read with sequence ID "ABC" appears as the 3rd record in the "Read 1" FASTQ file, it must also be the 3rd record in the "Read 2" FASTQ file. The disclosed method ensures this happens seamlessly.

Once a read and its mate are available, the memory should be freed and each read written to its corresponding FASTQ file. This will ensure that the output FASTQ files are roughly "sorted by alignment" and will compress better than the original "pseudo-random order" FASTQ file from the sequencing software. In other words, the regenerated FASTQ files output by the systems and methods disclosed herein are smaller than those typically generated by the original input FASTQ file generated by DNA sequencing software. It is noted that although the order of reads from the sequencer of the original FASTQ file is "pseudo-random," this is typically a result of the physical coordinates of the molecule being sequenced with respect to the flowcell. For example, all reads from a specific tile are grouped together. This can be seen when looking at the FASTQ "header" record, which includes the tile number and the X-Y coordinates of the cluster within the tile. The actual "SEQ" and "QUAL" columns of the FASTQ record (ignoring the header) suggest the order does appear to be random, as this reflects the random process of molecules falling on different physical coordinates of the flowcell. Therefore, although the reads is not actually random, as used herein, the order appears pseudo-random.

Instead, at decision 2040, if using single-ended sequencing data, necessary information (e.g., three or four fields of the FASTQ format) is written to the FASTQ file as it is encountered in the compressed SAM file, which is sorted by alignment (step 2060). This will ensure that the output FASTQ file will be "sorted by alignment" and will compress better than the original "pseudo-random order" FASTQ file from the sequencing software.

The resultant FASTQ file (from either step 2050/2060) is compressed (at step 2070). This compressed FASTQ file is smaller than the original input FASTQ file due to the decreased entropy of FASTQ records that have been re-ordered to "sorted by alignment", allowing for similar/overlapping reads to fall in the same compression window.

Finally, at step 2080, the FQSUM checksum is used, which, as discussed, is invariant to the order of FASTQ records to ensure that the FQSUM checksum of the FASTQ files output is identical to the original input FASTQ files that were originally created by sequencing software, which FQSUM was also stored in the SAM file header at step 1010. This checksum process does not require any pre-sorting or re-ordering of FASTQ records, making it ideal for large data sets.

Hardware and Software

According to various embodiments, various functionality discussed herein can be performed by and/or with the help of one or more computers. Such a computer can be and/or incorporate, as just some examples, a personal computer, a server, a smartphone, a system-on-a-chip, and/or a microcontroller. Such a computer can, in various embodiments, run Linux, MacOS, Windows, or another operating system.

Such a computer can also be and/or incorporate one or more processors operatively connected to one or more memory or storage units, wherein the memory or storage may contain data, algorithms, and/or program code, and the processor or processors may execute the program code and/or manipulate the program code, data, and/or algorithms. Shown in FIG. 12 is an example computer employable in various embodiments of the present invention. Exemplary computer 1201 includes system bus 1203 which operatively connects two processors 1205 and 1207, random access memory (RAM) 1209, read-only memory (ROM) 1211, input output (I/O) interfaces 1213 and 1215, storage interface 1217, and display interface 1219. Storage interface 1217 in turn connects to mass storage 1221. Each of I/O interfaces 1213 and 1215 can, as just some examples, be a Universal Serial Bus (USB), a Thunderbolt, an Ethernet, a Bluetooth, a Long-Term Evolution (LTE), a 5G, an IEEE 488, and/or other interface. Mass storage 1221 can be a flash drive, a hard drive, an optical drive, or a memory chip, as just some possibilities. Processors 1205 and 1207 can each be, as just some examples, a commonly known processor such as an ARM-based or x86-based processor. Computer 1201 can, in various embodiments, include or be connected to a touch screen, a mouse, and/or a keyboard. Computer 1201 can additionally include or be attached to card readers, DVD drives, floppy disk drives, hard drives, memory cards, ROM, and/or the like whereby media containing program code (e.g., for performing various operations and/or the like described herein) may be inserted for the purpose of loading the code onto the computer.

In accordance with various embodiments of the present invention, a computer may run one or more software modules designed to perform one or more of the above-described operations. Such modules can, for example, be programmed using Python, Java, JavaScript, Swift, C, C++, C#, and/or another language. Corresponding program code can be placed on media such as, for example, DVD, CD-ROM, memory card, and/or floppy disk. It is noted that any indicated division of operations among particular software modules is for purposes of illustration, and that alternate divisions of operation may be employed. Accordingly, any operations indicated as being performed by one software module can instead be performed by a plurality of software modules. Similarly, any operations indicated as being performed by a plurality of modules can instead be performed by a single module. It is noted that operations indicated as being performed by a particular computer can instead be performed by a plurality of computers. It is further noted that, in various embodiments, peer-to-peer and/or grid computing techniques may be employed. It is additionally noted that, in various embodiments, remote communication among software modules may occur. Such remote communication can, for example, involve JavaScript Object Notation-Remote Procedure Call (JSON-RPC), Simple Object Access Protocol (SOAP), Java Messaging Service (JMS), Remote Method Invocation (RMI), Remote Procedure Call (RPC), sockets, and/or pipes.

Moreover, in various embodiments the functionality discussed herein can be implemented using special-purpose circuitry, such as via one or more integrated circuits, Application Specific Integrated Circuits (ASICs), or Field Programmable Gate Arrays (FPGAs). A Hardware Description Language (HDL) can, in various embodiments, be employed in instantiating the functionality discussed herein. Such an HDL can, as just some examples, be Verilog or Very High-Speed Integrated Circuit Hardware Description Language (VHDL). More generally, various embodiments can be implemented using hardwired circuitry without or without software instructions. As such, the functionality discussed herein is limited neither to any specific combination of hardware circuitry and software, nor to any particular source for the instructions executed by the data processing system.

What is claimed is:

1. A method of regenerating a FASTQ file from a compressed sequence alignment map file, the compressed sequence alignment map file including alignment data for a plurality of sequence strings for more than one aligned reads of clusters on a flow cell, the method comprising:

(a) determining an fqsum of an original FASTQ file on which the compressed sequence alignment file is based, wherein each entry of the original FASTQ file is defined by at least four line-separated fields per sequence and the fqsum represents an order invariant checksum of the original FASTQ file;

(b) storing a quality score of each base call for individual instances of the plurality of sequence strings;

(c) sorting the compressed sequence alignment map file by one or more reference genome coordinates;

(d) extracting primary alignments from the compressed sequence alignment map file;

(e) ensuring all FASTQ records from the original FASTQ file are stored in the compressed SAM file;

(f) reconstructing original base quality scores by at least one of retrieving the stored quality score or applying an inverse of a model of the stored quality score;

(g) writing at least three of the four line-separated fields per sequence of the compressed sequence alignment map file to a regenerated FASTQ file; and (h) compressing the regenerated FASTQ file.

2. The method of claim 1, further comprising comparing the determined fqsum with an fqsum of the regenerated FASTQ file.

3. The method of claim 1, wherein said determining the fqsum of the original FASTQ file further comprises: for a set A and a set B of the original FASTQ file, fqsum ({A}) =fqsum (fqsum ({A})), fqsum ({A, B})=fqsum ({B, A}), and fqsum({fqsum ({A, B}), C})=fqsum ({A, fqsum({B, C})}).

4. The method of claim 1, wherein said storing the quality score comprises generating a base quality score recalibration model.

5. The method of claim 1, wherein said storing the quality score of each base call for individual instances of the plurality of sequence strings comprises storing a Phred scaled score.

6. The method of claim 5, wherein said storing the quality score of each base call for individual instances of the plurality of sequence strings comprises storing a string of integers, equal in length to a selected sequence string of the plurality of sequence strings.

7. The method of claim 1, wherein said ensuring all FASTQ records from the original FASTQ file are stored in the compressed SAM file further comprises: (i) removing sequencing duplicates and off-target reads, and (ii) storing the sequencing duplicates and off-target reads in an auxiliary compressed sequence alignment map file.

8. The method of claim 1, wherein the at least four line-separated fields per sequence of each entry of the original FASTQ file comprises: (i) a sequence identifier field, (ii) a sequence field, (iii) a quality score identifier field, and (iv) a quality score field.

9. The method of claim 1, wherein the compressed sequence alignment map file comprises at least one of a binary alignment map file and a compressed reference-oriented map file.

10. The method of claim 1, wherein a file size of the compressed sequence alignment map file is smaller than a file size of either of the original FASTQ file and the regenerated FASTQ file.

11. A method of regenerating a FASTQ file from a compressed sequence alignment map file, the compressed sequence alignment map file including alignment data for a plurality of sequence strings for more than one aligned reads of clusters on a flow cell, the method comprising:

(a) determining an fqsum of an original FASTQ file on which the compressed sequence alignment file is based, wherein each entry of the original FASTQ file is defined by at least four line-separated fields per sequence and the fqsum represents an order invariant checksum of the original FASTQ file;

(b) storing a quality score of each base call for individual instances of the plurality of sequence strings;

(c) sorting the compressed sequence alignment map file by sequence string;

(d) extracting primary alignments from the compressed sequence alignment map file;

(e) ensuring all FASTQ records from the original FASTQ file are stored in the compressed SAM file;

(f) reconstructing original base quality scores by at least one of retrieving the stored quality score or applying an inverse of a model of the stored quality score;

(g) writing at least three of the four line-separated fields per sequence of the compressed sequence alignment map file to a regenerated FASTQ file; and (h) compressing the regenerated FASTQ file.

12. The method of claim 11, further comprising comparing the determined fqsum with an fqsum of the regenerated FASTQ file.

13. The method of claim 11, wherein said determining the fqsum of the original FASTQ file further comprises: for a set A and a set B of the original FASTQ file, fqsum ({A})= fqsum (fqsum ({A})), fqsum ({A, B})=fqsum ({B, A}), and fqsum({fqsum ({A, B}), C})=fqsum ({A, fqsum({B, C})}).

14. The method of claim 11, wherein said storing the quality score comprises generating a base quality score recalibration model.

15. The method of claim 11, wherein said storing the quality score of each base call for individual instances of the plurality of sequence strings comprises storing a Phred scaled score.

16. The method of claim 15, wherein said storing the quality score of each base call for individual instances of the plurality of sequence strings comprises storing a string of integers, equal in length to a selected sequence string of the plurality of sequence strings.

17. The method of claim 11, wherein the at least four line-separated fields per sequence of each entry of the original FASTQ file comprises: (i) a sequence identifier field, (ii) a sequence field, (iii) a quality score identifier field, and (iv) a quality score field.

18. The method of claim 10, wherein the compressed sequence alignment map file comprises at least one of a binary alignment map file and a compressed reference-oriented map file.

19. The method of claim 11, wherein a file size of the compressed sequence alignment map file is smaller than a file size of either of the original FASTQ file and the regenerated FASTQ file.

20. A computer program product for regenerating a FASTQ file from a compressed sequence alignment map file, the compressed sequence alignment map file including alignment data for a plurality of sequence strings for more than one aligned reads of clusters on a flow cell, the computer program product being encoded on one or more machine-readable storage media and comprising instructions for:

(i) determining an fqsum of an original FASTQ file on which the compressed sequence alignment file is based, wherein each entry of the original FASTQ file is defined by at least four line-separated fields per sequence and the fqsum represents an order invariant checksum of the original FASTQ file;

(ii) storing a quality score of each base call for individual instances of the plurality of sequence strings;

(iii) sorting the compressed sequence alignment map file by one or more reference genome coordinates;

(iv) extracting primary alignments from the compressed sequence alignment map file;

(v) ensuring all FASTQ records from the original FASTQ file are stored in the compressed SAM file;

(vi) reconstructing original base quality scores by at least one of retrieving the stored quality score or applying an inverse of a model of the stored quality score;

(vii) writing at least three of the four line-separated fields per sequence of the compressed sequence alignment map file to a regenerated FASTQ file; and (viii) compressing the regenerated FASTQ file.

* * * * *